US006716831B1

(12) United States Patent
Breault et al.

(10) Patent No.: US 6,716,831 B1
(45) Date of Patent: Apr. 6, 2004

(54) 2,4-DIAMINO-PYRIMIDINE DEPRIVATIVES HAVING ANTI-CELL PROLIFERATIVE ACTIVITY

(75) Inventors: Gloria A. Breault, Macclesfield (GB); Stewart R. James, Macclesfield (GB); Janet E. Pease, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/914,788

(22) PCT Filed: Mar. 2, 2000

(86) PCT No.: PCT/GB00/00737

§ 371 (c)(1),
(2), (4) Date: Nov. 15, 2001

(87) PCT Pub. No.: WO00/53595

PCT Pub. Date: Sep. 14, 2000

(30) Foreign Application Priority Data

Mar. 6, 1999 (GB) .............................................. 9905075

(51) Int. Cl.$^7$ ...................... A61K 31/33; A61K 31/405; C07D 239/02; C07D 403/00
(52) U.S. Cl. ........................ 514/183; 514/275; 514/415; 544/309; 544/310
(58) Field of Search ................................ 514/183, 275, 514/415; 544/309, 310

(56) References Cited

U.S. PATENT DOCUMENTS

| 4,983,608 | A | 1/1991 | Effland et al. ............... 514/216 |
| 5,516,775 | A | 5/1996 | Zimmermann et al. .. 514/224.2 |
| 5,610,303 | A | 3/1997 | Kimura et al. ............... 544/326 |
| 5,739,143 | A | 4/1998 | Adams et al. ............... 514/275 |
| 5,859,041 | A | 1/1999 | Liverton et al. ............ 514/396 |

FOREIGN PATENT DOCUMENTS

| CA | 2231765 | | 9/1998 |
|---|---|---|---|
| EP | 0 363 002 | | 4/1990 |
| EP | 0 379 806 | B1 | 8/1990 |
| EP | 0 945 443 | A1 | 9/1999 |
| WO | WO 91/18887 | | 12/1991 |
| WO | WO 92/20642 | | 11/1992 |
| WO | WO 95/09847 | | 4/1995 |
| WO | WO 95/09851 | | 4/1995 |
| WO | WO 95/09852 | | 4/1995 |
| WO | 9509852 | * | 4/1995 |
| WO | WO 95/09853 | | 4/1995 |
| WO | WO 95/15952 | | 6/1995 |
| WO | WO 96/05177 | | 2/1996 |
| WO | WO 96/28427 | | 9/1996 |
| WO | WO 96/40143 | | 12/1996 |
| WO | WO 97/19065 | | 5/1997 |
| WO | WO 97/35856 | | 10/1997 |
| WO | WO 97/47618 | | 12/1997 |
| WO | WO 98/11095 | | 3/1998 |
| WO | WO 98/16230 | | 4/1998 |
| WO | WO 98/18782 | | 5/1998 |
| WO | WO 98/25619 | | 6/1998 |
| WO | WO 98/33798 | | 8/1998 |
| WO | WO 98/41512 | | 9/1998 |
| WO | WO 98/54093 | | 12/1998 |
| WO | WO 98/56788 | | 12/1998 |
| WO | WO 99/01136 | | 1/1999 |
| WO | WO 99/32121 | | 1/1999 |
| WO | WO 99/18942 | | 4/1999 |
| WO | WO 99/31073 | | 6/1999 |
| WO | WO 99/50250 | | 10/1999 |
| WO | WO 00/12485 | | 3/2000 |
| WO | WO 00/12486 | | 3/2000 |
| WO | WO 00/17202 | | 3/2000 |
| WO | WO 00/17203 | | 3/2000 |
| WO | WO 00/25780 | | 5/2000 |
| WO | WO 00/26209 | | 5/2000 |
| WO | WO 00/44750 | | 8/2000 |
| WO | WO 00/49018 | | 8/2000 |
| WO | WO 00/53595 | | 9/2000 |
| WO | WO 00/55161 | | 9/2000 |
| WO | WO 00/59892 | | 10/2000 |
| WO | WO 00/78731 | A1 | 12/2000 |
| WO | WO 01/14375 | | 3/2001 |
| WO | WO 01/29009 | A1 | 4/2001 |
| WO | WO 01/30778 | A1 | 5/2001 |
| WO | WO 01/64653 | A1 | 9/2001 |
| WO | WO 01/64654 | A1 | 9/2001 |
| WO | WO 01/64655 | A1 | 9/2001 |
| WO | WO 01/64656 | A1 | 9/2001 |

OTHER PUBLICATIONS

Cecil Textbook of Medicine, W.B.Saunders CO, 1996, Edited by 7 Bennett & Plum, pp. 1004–1010.*

Uckun et al, "Structure–Based Design of Novel Anti–cancer Agts.", Current Cancer Drug Targets, 1,59–71(2001).*

McLean et al, PubMed Abstract 12562313, also cited as Expert Opin. Pharmacother., 4/2,227–34(2003).*

Kronberg L.J., PubMed Abstract 9790298, also cited as Head Neck, 20/8, 745–52(1998).*

El–Kerdawy et al.; 2,4–Bis (Substituted)–5–Nitropyrimidines of Expected Diuretic Action; Egypt J. Chem. vol. 29, No. 2, 1986, pp. 247–251.

Fiziol Akt Veshchestva, 1975, vol. 7, pp. 68–72.

(List continued on next page.)

Primary Examiner—Richard L. Raymond
Assistant Examiner—Sudhaker B. Patel
(74) Attorney, Agent, or Firm—Morgan, Lewis & Bockius LLP

(57) ABSTRACT

A pyrimidine derivative of formula (I) or (I'): wherein: $R^x$ is a substituent as defined within; $Q_1$ is optionally substituted phenyl, and $Q_1$ bears a substituent of formula (Ia) wherein: X, $Y^1$, $Y^2$, Z, n, and m are as defined within; —$NQ_2$ is an optionally substituted heterocyclic moiety containing one hydrogen heteroatom and optionally containing a further heteroatom; or a pharmaceutically acceptable salt in vivo hydrolysable ester thereof; are useful as anti-cancer agents. Processes for their manufacture and pharmaceutical compositions containing them are described.

11 Claims, No Drawings

OTHER PUBLICATIONS

Ghosh et al.; 2,4–Bis(arylamino)–5–methylpyrimidines as Antimicrobial Agents; J. Med. Chem., 1967, vol. 10, No. 5, pp. 974–975.

Ghosh, 2,4–Bis(Arylamino)–6–Methyl Pyrimidines as Antimicrobial Agents, J. Indian Chem. Soc., vol. 58, No. 5, 1981, pp. 512–513.

Ghosh, 2,4–Bis(arylamino)–6–methylpyrimidines as an antimicrobial agents, Chemical Abstract No. 97712f, vol. 95, 1981, pp. 648.

Schmidt et al.; "A Convenient Synthesis of 2–substituted 4–Amino–5–pyrimidinecarbonitriles"; J. Heterocycle Chem., 1997, vol. 24, No. 5, pp. 1305–1307.

* cited by examiner

2,4-DIAMINO-PYRIMIDINE DEPRIVATIVES HAVING ANTI-CELL PROLIFERATIVE ACTIVITY

This application is the National Phase of International Application PCT/GB00/00737 filed Mar. 2, 2000 which designated the U.S. and that International Application was published under PCT Article 21(2) in English.

The invention relates to pyrimidine derivatives, or pharmaceutically acceptable salts or in vivo hydrolysable esters thereof, which possess cell-cycle inhibitory activity and are accordingly useful for their anti cancer (such as anti-cell-proliferative, anti-cell migration and/or apoptotic) activity and are therefore useful in methods of treatment of the human or animal body. The invention also relates to processes for the manufacture of said pyrimidine derivatives, to pharmaceutical compositions containing them and to their use in the manufacture of medicaments of use in the production of an anti-cell-proliferation effect in a warm-blooded animal such as man.

A family of intracellular proteins called cyclins play a central role in the cell cycle. The synthesis and degradation of cyclins is tightly controlled such that their level of expression fluctuates during the cell cycle. Cyclins bind to cyclin-dependent serine/threonine kinases (CDKs) and this association is essential for CDK (such as CDK1, CDK2, CDK4 and/or CDK6) activity within the cell. Although the precise details of how each of these factors combine to regulate CDK activity is poorly understood, the balance between the two dictates whether or not the cell will progress through the cell cycle.

The recent convergence of oncogene and tumour suppressor gene research has identified regulation of entry into the cell cycle as a key control point of mitogenesis in tumours. Moreover, CDKs appear to be downstream of a number of oncogene signalling pathways. Disregulation of CDK activity by upregulation of cyclins and/or deletion of endogenous inhibitors appears to be an important axis between mitogenic signalling pathways and proliferation of tumour cells.

Accordingly it has been recognised that an inhibitor of cell cycle kinases, particularly inhibitors of CDK2, CDK4 and/or CDK6 (which operate at the S-phase, G1-S and G1-S phase respectively) should be of value as a selective inhibitor of cell proliferation, such as growth of mammalian cancer cells.

Furthermore, it is believed that inhibition of focal adhesion kinase (FAK), which is involved in signal transduction pathways, induces apoptosis (cell-death) and/or inhibits cell migration and an inhibitor of FAK may therefore have value as an anti-cancer agent.

The present invention is based on the discovery that certain pyrimidine compounds surprisingly inhibit the effects of cell cycle kinases showing selectivity for CDK2, CDK4 and CDK6, and also inhibit FAK and thus possess anti-cancer (anti-cell-migration/proliferation and/or apoptotic). Such properties are expected to be of value in the treatment of disease states associated with aberrant cell cycles and cell proliferation such as cancers (solid tumours and leukemias), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation.

According to the invention there is provided a pyrimidine derivative of the formula (I) or (I'):

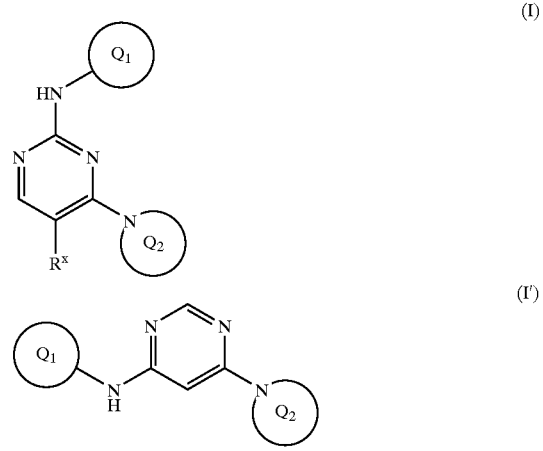

wherein:
$R^x$ is selected from hydrogen, halo, hydroxy, nitro, amino, $C_{1-3}$alkylamino, di-[$C_{1-3}$alkyl]amino, cyano, trifluoromethyl, trichloromethyl, $C_{1-3}$alkyl [optionally substituted by 1 or 2 substituents independently selected from halo, cyano, amino, $C_{1-3}$alkylamino, di-[$C_{1-3}$alkyl]amino, hydroxy and trifluoromethyl], $C_{3-5}$alkenyl [optionally substituted by up to three halo substituents, or by one trifluoromethyl substituent], $C_{3-5}$alkynyl, $C_{1-3}$alkoxy, —SH, —S—$C_{1-3}$alkyl, carboxy, $C_{1-3}$alkoxycarbonyl;

$Q_1$ is phenyl, and $Q_1$ bears on an available carbon atom not adjacent to the —NH— link one substituent of the formula (Ia), and —$NQ_2$ (defined hereinbelow) may optionally bear on any available carbon atom further substituents of the formula (Ia):

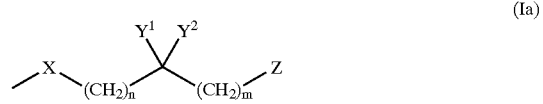

wherein:
X is —$CH_2$—, —O—, —NH—, —$NR^y$— or —S— [wherein $R^y$ is $C_{1-4}$alkyl, optionally substituted by one substituent selected from halo, amino, cyano, $C_{1-4}$alkoxy or hydroxy];
$Y^1$ is H, $C_{1-4}$alkyl or as defined for Z;
$Y^2$ is H or $C_{1-4}$alkyl;
Z is $R^aO$—, $R^bR^cN$—, $R^dS$—, $R^eR^fNNR^g$—, a nitrogen linked heteroaryl or a nitrogen linked heterocycle [wherein said heterocycle is optionally substituted on a ring carbon or a ring nitrogen by $C_{1-4}$alkyl or $C_{1-4}$alkanoyl] wherein $R^a$, $R^b$, $R^c$, $R^d$, $R^e$, $R^f$ and $R^g$ are independently selected from hydrogen, $C_{1-4}$alkyl, $C_{2-4}$alkenyl, $C_{3-8}$cycloalkyl, and wherein said $C_{1-4}$alkyl and $C_{2-4}$alkenyl are optionally substituted by one or more phenyl;
n is 1, 2 or 3;
m is 1, 2 or 3;
and —$NQ_2$ is an unquaternised N-linked 5-, 6- or 7-membered monocyclic heterocyclic moiety containing one nitrogen heteroatom and optionally containing a further one or two heteroatoms selected from nitrogen, oxygen and sulphur or —$NQ_2$ is an unquaternised N-linked 8-, 9- or 10-membered bicyclic heterocyclic moiety containing one or two nitrogen heteroatoms and optionally containing a further one or two heteroatoms selected from nitrogen, oxygen and sulphur and wherein if said heterocyclic moiety contains an —NH— moiety that nitrogen may be optionally substituted by a group selected from $C_{1-6}$alkyl, $C_{1-6}$alkanoyl, $C_{1-6}$alkylsulphonyl, $C_{1-6}$alkoxycarbonyl, benzyl, benzoyl or phenylsulphonyl; and $Q_1$ and —$NQ_2$ may optionally and independently bear on any available carbon atom up to four substituents independently selected from halo, hydroxy, thio, nitro, carboxy, cyano, $C_{2-4}$alkenyl [optionally substituted by up to three halo substituents, or by one trifluoromethyl substituent], $C_{2-4}$alkynyl, $C_{1-5}$alkanoyl, $C_{1-4}$alkoxycarbonyl, $C_{1-6}$alkyl, hydroxy-$C_{1-3}$alkyl, fluoro-$C_{1-4}$alkyl, amino-$C_{1-3}$alkyl, $C_{1-4}$alkylamino-$C_{1-3}$alkyl, di-[$C_{1-4}$alkyl]amino-$C_{1-3}$alkyl, cyano-$C_{1-4}$alkyl, $C_{2-4}$alkanoyloxy-$C_{1-4}$-alkyl, $C_{1-4}$alkoxy-$C_{1-3}$alkyl, carboxy-$C_{1-4}$alkyl, $C_{1-4}$alkoxycarbonyl-$C_{1-4}$alkyl, carbamoyl-$C_{1-4}$alkyl, N-$C_{1-4}$alkylcarbamoyl-$C_{1-4}$alkyl, N,N-di-[$C_{1-4}$ alkyl]-carbamoyl-$C_{1-4}$alkyl, pyrrolidin-1-yl-$C_{1-3}$alkyl, piperidin-1-yl-$C_{1-3}$alkyl, piperazin-1-yl-$C_{1-3}$alkyl, morpholino-$C_{1-3}$alkyl, thiomorpholino-$C_{1-3}$alkyl, imidazo-1-yl-$C_{1-3}$alkyl, piperazin-1-yl, morpholino, thiomorpholino, $C_{1-4}$alkoxy, cyano-$C_{1-4}$alkoxy, carbamoyl-$C_{1-4}$alkoxy, N-$C_{1-4}$alkylcarbamoyl-$C_{1-4}$alkoxy, N,N-di-[$C_{1-4}$alkyl]-carbamoyl-$C_{1-4}$alkoxy, 2-aminoethoxy, 2-$C_{1-4}$alkylaminoethoxy, 2-di-[$C_{1-4}$alkyl]aminoethoxy, $C_{1-4}$alkoxycarbonyl-$C_{1-4}$ alkoxy, halo-$C_{1-4}$alkoxy, 2-hydroxyethoxy, $C_{2-4}$alkanoyloxy-$C_{2-4}$alkoxy, 2-$C_{1-4}$alkoxyethoxy, carboxy-$C_{1-4}$alkoxy, 2-pyrrolidin-1-yl-ethoxy, 2-piperidino-ethoxy, 2-piperazin-1-yl-ethoxy, 2-morpholino-ethoxy, 2-thiomorpholino-ethoxy, 2-imidazo-1-yl-ethoxy, $C_{3-5}$alkenyloxy, $C_{3-5}$alkynyloxy, $C_{1-4}$alkylthio, $C_{1-4}$alkylsulphinyl, $C_{1-4}$alkylsulphonyl, hydroxy$C_{2-4}$alkylthio, hydroxy$C_{2-4}$alkylsulphinyl, hydroxy $C_{2-4}$alkylsulphonyl, ureido ($H_2N$—CO—NH—), $C_{1-4}$alkylNH—CO—NH—, di-[$C_{1-4}$alkyl]N—CO—NH—, $C_{1-4}$alkylNH—CO—N[$C_{1-4}$alkyl]-, di-[$C_{1-4}$alkyl]N—CO—N[$C_{1-4}$alkyl]-, carbamoyl, N-[$C_{1-4}$alkyl]carbamoyl, N,N-di-[$C_{1-4}$alkyl] carbamoyl, amino, $C_{1-4}$alkylamino, di-[$C_{1-4}$alkyl] amino, $C_{2-4}$alkanoylamino, sulphamoyl, N-($C_{1-4}$alkyl)sulphamoyl, N,N-di-($C_{1-4}$alkyl)sulphamoyl, and also independently, or where appropriate in addition to, the above optional substituents, $Q_1$ and —$NQ_2$ may optionally and independently bear on any available carbon atom up to two further substituents independently selected from $C_{3-8}$cycloalkyl, phenyl-$C_{1-4}$alkyl, phenyl-$C_{1-4}$alkoxy, phenylthio, phenyl, naphthyl, benzoyl, phenoxy, benzimidazol-2-yl, and a 5- or 6-membered aromatic heterocycle (linked via a ring carbon atom and containing one to three heteroatoms independently selected from oxygen, sulphur and nitrogen); wherein said naphthyl, phenyl, benzoyl, phenoxy, 5- or 6-membered aromatic heterocyclic substituents and the phenyl group in said phenyl-$C_{1-4}$alkyl, phenylthio and phenyl-$C_{1-4}$alkoxy substituents may optionally bear one or two substituents independently selected from halo, $C_{1-4}$alkyl and $C_{1-4}$alkoxy;

or a pharmaceutically acceptable salt or in vivo hydrolysable ester thereof.

A suitable value for —$NQ_2$ as an unquaternised N-linked 5-, 6- or 7-membered monocyclic heterocyclic moiety containing one nitrogen heteroatom and optionally containing a further one or two heteroatoms selected from nitrogen, oxygen and sulphur; is a monocyclic heterocyclic moiety containing (before linkage to the pyrimidine ring in (I) or (I')) a free —NH, such as pyrrole, 2-pyrroline, 3-pyrroline, pyrrolidine, imidazole, imidazoline, imidazolidine, pyrazole, pyrazoline, pyrazolidine, triazole, piperidine, morpholine, thiomorpholine, piperazine, homopiperazine or homopiperidine.

A suitable value for —$NQ_2$ as an unquaternised N-linked 8-, 9- or 10-membered bicyclic heterocyclic moiety containing one or two nitrogen heteroatoms and optionally containing a further one or two heteroatoms selected from nitrogen, oxygen and sulphur; is a bicyclic heterocyclic moiety containing (before linkage to the pyrimidine ring in (I) or (I')) a free —NH, such as 1H-imidazo[1,2-a]pyrrole, indole, isoindole, indoline, isoindazole (benzpyrazole), benzimidazole or purine (or a partially or fully hydrogenated version of any of these); or a partially or fully saturated aromatic heterocycle containing (before linkage to the pyrimidine ring in (I) or (I')) a free —NH, for example, partially or fully saturated derivatives of quinolyl (such as 1,2-dihydroquinolinyl or 1,2,3,4-tetrahydroquinolinyl), isoquinolyl, cinnolinyl, quinazolinyl, quinoxalinyl, phthalazinyl, naphthyridinyl, benzoxazole, benzothiazole, imidazo[1,2-a]pyridine, imidazo[1,5-a]pyridine, imidazo[1,2-c]pyrimidine, imidazo[1,2-a]pyrimidine, imidazo[1,5-a]pyrimidine, imidazo[1,2-a]pyrazine or imidazo[1,5-a]pyrazine or 4,5,6,7-tetrahydrothieno[2,3-c]pyridin-6-yl.

For —$NQ_2$ as an unquaternised N-linked 8-, 9- or 10-membered bicyclic heterocyclic moiety containing one or two nitrogen heteroatoms (and optionally containing a further one or two heteroatoms selected from nitrogen, oxygen and sulphur), the link to the pyrimidine ring in (I) or (I') may be via a nitrogen atom in either of the two rings of the bicyclic heterocyclic moiety, provided that the ring system remains unquaternised.

Conveniently —$NQ_2$ is, for example, indole, isoindole, indoline, isoindazole (benzpyrazole), benzimidazole, purine or 1,2,3,4-tetrahydroquinolinyl.

Alternatively, —$NQ_2$ is, for example, indole, indoline, benzimidazole, 1,2,3,4-tetrahydroquinolinyl piperazine or morpholine.

A suitable value for a ring substituent when it is a 5- or 6-membered aromatic heterocycle (linked via a ring carbon atom and containing one to three heteroatoms independently selected from oxygen, sulphur and nitrogen) is, for example, pyrrole, furan, thiophene, imidazole, oxazole, isoxazole, thiazole, pyridyl, pyridazinyl, pyrimidinyl, pyrazinyl or p-isoxazine.

A suitable value for Z in group (Ia) when it is a "nitrogen linked heteroaryl" is a mono or bicyclic ring that has a degree of unsaturation, containing 4–12 atoms, at least one of which is selected from nitrogen, and optionally 1–3 further atoms are selected from nitrogen, sulphur or oxygen, wherein a —$CH_2$— group can optionally be replaced by a —C(O)—, and a ring sulphur and/or nitrogen atom may be optionally oxidised to form S-oxide(s) and/or an N-oxide. Suitably "nitrogen linked heteroaryl" is a monocyclic ring containing 5 or 6 atoms or a bicyclic ring containing 9 or 10 atoms. The nitrogen link results in a neutral compound being formed. Suitable values for "nitrogen linked heteroaryl" include imidazol-1-yl, pyrrolin-1-yl, imidazolin-1-yl, pyrazolin-1-yl, triazol-1-yl, indol-1-yl, isoindol-2-yl, indolin-1-yl, benzimidazol-1-yl, pyrrol-1-yl or pyrazol-1-yl. Preferably "nitrogen linked heteroaryl" is imidazol-1-yl.

A suitable value for Z in group (Ia) when it is a "nitrogen linked heterocycle" is an unsaturated mono or bicyclic ring that contains 4–12 atoms, at least one of which is selected from nitrogen, and optionally 1–3 further atoms are selected from nitrogen, sulphur or oxygen, wherein a —CH$_2$— group can optionally be replaced by a —C(O)—, and a ring sulphur may be optionally oxidised to form S-oxide(s). Suitably "nitrogen linked heterocycle" is a monocyclic ring containing 5 or 6 atoms or a bicyclic ring containing 9 or 10 atoms. Suitable values for "nitrogen linked heterocycle" include pyrrolidin-1-yl, piperidino, piperazin-1-yl, morpholino, thiomorpholino, homopiperidin-y-1 or homopiperazin-1-yl. Preferably a "nitrogen linked heterocycle" is pyrrolidin-1-yl, piperazin-1-yl or morpholino.

In this specification the term "alkyl" includes both straight and branched chain alkyl groups but references to individual alkyl groups such as "propyl" are specific for the straight chain version only. An analogous convention applies to other generic terms.

Suitable values for the generic radicals (such as in substituents on $Q_1$ and —NQ$_2$) referred to above include those set out below:

when it is halo is, for example, fluoro, chloro, bromo and iodo; $C_{2-4}$alkenyl is, for example, vinyl and allyl; when it is $C_{3-5}$alkenyl is, for example, allyl and buten-3-yl; when it is $C_{3-5}$alkynyl is, for example, propyn-2-yl; when it is $C_{2-4}$alkynyl is, for example, ethynyl and propyn-2-yl; when it is $C_{1-5}$alkanoyl is, for example, formyl and acetyl; when it is $C_{1-3}$alkoxycarbonyl is, for example, methoxycarbonyl, ethoxycarbonyl and propoxycarbonyl; when it is $C_{1-4}$alkoxycarbonyl is, for example, methoxycarbonyl, ethoxycarbonyl, propoxycarbonyl and tert-butoxycarbonyl; when it is $C_{1-3}$alkyl is, for example, methyl, ethyl, propyl, isopropyl; when it is $C_{1-4}$alkyl is, for example, methyl, ethyl, propyl, isopropyl, butyl, isobutyl, sec-butyl or tert-butyl; when it is $C_{1-6}$alkyl is, for example, methyl, ethyl, propyl, isopropyl, butyl, isobutyl, sec-butyl, tert-butyl, 3-methylbutyl or hexyl; when it is hydroxy-$C_{1-3}$alkyl is, for example, hydroxymethyl, 1-hydroxyethyl, 2-hydroxyethyl and 3-hydroxypropyl; when it is fluoro-$C_{1-4}$alkyl is, for example, fluoromethyl, difluoromethyl, trifluoromethyl and 2-fluoroethyl; when it is amino-$C_{1-3}$alkyl is, for example, aminomethyl, 1-aminoethyl and 2-aminoethyl; when it is $C_{1-4}$alkylamino-$C_{1-3}$-alkyl is, for example, methylaminomethyl, ethylaminomethyl, 1-methylaminoethyl, 2-methylaminoethyl, 2-ethylamimoethyl and 3-methylaminopropyl; when it is di-[$C_{1-4}$alkyl]amino-$C_{1-3}$alkyl is, for example, dimethylaminomethyl, diethylaminomethyl, 1-dimethylaminoethyl, 2-dimethylaminoethyl and 3-dimethylaminopropyl; when it is cyano-$C_{1-4}$alkyl is, for example cyanomethyl, 2-cyanoethyl and 3-cyanopropyl; when it is $C_{2-4}$alkanoyloxy-$C_{1-4}$-alkyl is, for example, acetoxymethyl, propionyloxymethyl, butyryloxymethyl, 2-acetoxyethyl and 3-acetoxypropyl; when it is $C_{1-4}$alkoxy-$C_{1-3}$alkyl is, for example, methoxymethyl, ethoxymethyl, 1-methoxyethyl, 2-methoxyethyl, 2-ethoxyethyl and 3-methoxypropyl; when it is carboxy-$C_{1-4}$alkyl is, for example carboxymethyl, 1-carboxyethyl, 2-carboxyethyl and 3-carboxypropyl; when it is $C_{1-4}$alkoxycarbonyl-$C_{1-4}$alkyl is, for example, methoxycarbonylmethyl, ethoxycarbonylmethyl, tert-butoxycarbonylmethyl, 1-methoxycarbonylethyl, 1-ethoxycarbonylethyl, 2-methoxycarbonylethyl, 2-ethoxycarbonylethyl, 3-methoxycarbonylpropyl and 3-ethoxycarbonylpropyl; when it is carbamoyl-$C_{1-4}$alkyl is, for example carbanoylmethyl, 1-carbamoylethyl, 2-carbamoylethyl and 3-carbamoylpropyl; when it is N-$C_{1-4}$alkylcarbamoyl-$C_{1-4}$alkyl is, for example, N-methylcarbamoylmethyl, N-ethylcarbamoylmethyl, N-propylcarbamoylmethyl, 1-(N-methylcarbamoyl)ethyl, 1-(N-ethylcarbamoyl)ethyl, 2-(N-methylcarbamoyl)ethyl, 2-(N-ethylcarbamoyl)ethyl and 3-(N-methylcarbamoyl)propyl; when it is N,N-di-[$C_{1-4}$alkyl]-carbamoyl-$C_{1-4}$alkyl is, for example, N,N-dimethylcarbamoylmethyl, N-ethyl-N-methylcarbamoylmethyl, N,N-diethylcarbamoylmethyl, 1-(N,N-dimethylcarbamoyl)ethyl, 1-(N,N-diethylcarbamoyl)ethyl, 2-(N,N-dimethylcarbamoyl)ethyl, 2-(N,N-diethylcarbamoyl)ethyl and 3-(N,N-dimethylcarbamoyl)propyl; when it is pyrrolidin-1-yl-$C_{1-3}$alkyl is, for example, pyrrolidin-1-ylmethyl and 2-pyrrolidin-1-ylethyl; when it is piperidin-1-yl-$C_{1-3}$alkyl is, for example, piperidin-1-ylmethyl and 2-piperidin-1-ylethyl; when it is piperazin-1-yl-$C_{1-3}$alkyl is, for example, piperazin-1-ylmethyl and 2-piperazin-1-ylethyl; when it is morpholino-$C_{1-3}$alkyl is, for example, morpholinomethyl and 2-morpholinoethyl; when it is thiomorpholino-$C_{1-3}$alkyl is, for example, thiomorpholinomethyl and 2-thiomorpholinoethyl;

when it is imidazo-1-yl-$C_{1-3}$alkyl is, for example, imidazo-1-ylmethyl and 2-imidazo-1-ylethyl; when it is $C_{1-3}$alkoxy is, for example, methoxy, ethoxy, propoxy or isopropoxy; when it is $C_{1-4}$alkoxy is, for example, methoxy, ethoxy, propoxy, isopropoxy or butoxy; when it is cyano-$C_{1-4}$alkoxy is, for example, cyanomethoxy, 1-cyanoethoxy, 2-cyanoethoxy and 3-cyanopropoxy; when it is carbamoyl-$C_{1-4}$alkoxy is, for example, carbamoylmethoxy, 1-carbamoylethoxy, 2-carbamoylethoxy and 3-carbamoylpropoxy; when it is N-$C_{1-4}$alkylcarbamoyl-$C_{1-4}$alkoxy is, for example, N-methylcarbamoylmethoxy, N-ethylcarbamoylmethoxy, 2-(N-methylcarbamoyl)ethoxy, 2-(N-ethylcarbamoyl)ethoxy and 3-(N-methylcarbamoyl)propoxy; when it is N,N-di-[$C_{1-4}$alkyl]-carbamoyl-$C_{1-4}$alkoxy is, for example, N,N-dimethylcarbamoylmethoxy, N-ethyl-N-methylcarbamoylmethoxy, N,N-diethylcarbamoylmethoxy, 2-(N,N-dimethylcarbamoyl)ethoxy, 2-(N,N-diethylcarbamoyl)ethoxy and 3-(N,N-dimethylcarbamoyl)propoxy; when it is 2-$C_{1-4}$alkylaminoethoxy is, for example, 2-(methylamino)ethoxy, 2-(ethylamino)ethoxy and 2-(propylamino)ethoxy; when it is 2-di-[$C_{1-4}$alkyl]aminoethoxy is, for example, 2-(dimethylamino)ethoxy, 2-(N-ethyl-N-methylamino)ethoxy, 2-(diethylamino)ethoxy and 2-(dipropylamino)ethoxy; when it is $C_{1-4}$alkoxycarbonyl-$C_{1-4}$alkoxy is, for example, methoxycarbonylmethoxy, ethoxycarbonylmethoxy, 1-methoxycarbonylethoxy, 2-methoxycarbonylethoxy, 2-ethoxycarbonylethoxy and 3-methoxy-carbonylpropoxy; when it is halo-$C_{1-4}$alkoxy is, for example, difluoromethoxy, trifluoromethoxy, 2-fluoroethoxy, 2-chloroethoxy, 2-bromoethoxy, 3-fluoropropoxy and 3-chloropropoxy; when it is $C_{2-4}$alkanoyloxy-$C_{2-4}$alkoxy is, for example, 2-acetoxyethoxy, 2-propionyloxyethoxy, 2-butyryloxyethoxy and 3-acetoxypropoxy; when it is 2-$C_{1-4}$alkoxyethoxy is, for example, 2-methoxyethoxy, 2-ethoxyethoxy; when it is carboxy-$C_{1-4}$alkoxy is, for example, carboxymethoxy, 1-carboxyethoxy, 2-carboxyethoxy and 3-carboxypropoxy; when it is $C_{3-5}$alkenyloxy is, for example, allyloxy; when it is $C_{3-5}$alkynyloxy is, for example, propynyloxy; when it is $C_{1-4}$alkylthio is, for example, methylthio, ethylthio or propylthio; when it is $C_{1-4}$alkylsulphinyl is, for example, methylsulphinyl, ethylsulphinyl or propylsulphinyl; when it is $C_{1-4}$alkylsulphonyl is, for example, methylsulphonyl, ethylsulphonyl or propylsulphonyl; when it is N-$C_{1-4}$alkylcarbamoyl is, for example N-methylcarbamoyl, N-ethylcarbamoyl and N-propylcarbamoyl; when it is N,N-di-[$C_{1-4}$alkyl]-carbamoyl is, for example N,N-dimethylcarbamoyl, N-ethyl-N-methylcarbamoyl and N,N-diethylcarbamoyl; when it is $C_{1-4}$alkylamino or $C_{1-3}$alkylamino is, for example, methylamino, ethylamino or propylamino; when it is di-[$C_{1-4}$alkyl]amino or di-[$C_{1-3}$alkyl]amino is, for example, dimethylamino, N-ethyl-N-methylamino, diethylamino, N-methyl-N-propylamino or dipropylamino; when it is $C_{2-4}$alkanoylamino is, for example, acetamido, propionamido or butyramido; when it is phenyl-$C_{1-4}$alkyl is, for example benzyl or 2-phenylethyl; when it is phenyl-$C_{1-4}$alkoxy is, for example benzyloxy; when it is $C_{3-8}$cycloalkyl is, for example, cyclopropyl, cyclopentyl or cyclohexyl; when it is hydroxy$C_{2-4}$alkylthio is, for example, 2-hydroxyethylthio or 2-hydroxylpropylthio; when it is hydroxy$C_{2-4}$alkylsulphinyl is, for example, 2-hydroxyethylsulphinyl or 2-hydroxylpropylsulphinyl; when it is hydroxy$C_{2-4}$alkylsulphonyl is, for example, 2-hydroxyethylsulphonyl or 2-hydroxylpropylsulphonyl; when it is N-($C_{1-4}$alkyl)sulphamoyl is, for example, N-methylsulphamoyl or N-ethylsulphamoyl; when it is N,N-di-($C_{1-4}$alkyl)sulphamoyl is, for example, N,N-dimethylsulphamoyl, N-ethyl-N-methylsulphamoyl and N,N-diethylsulphamoyl.

A suitable pharmaceutically acceptable salt of a pyrimidine derivative of the invention is, for example, an acid-addition salt of a pyrimidine derivative of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically acceptable salt of a pyrimidine derivative of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

The compounds of the formula (I) or (I') may be administered in the form of a pro-drug which is broken down in the human or animal body to give a compound of the formula (I) or (I'). Examples of pro-drugs include in vivo hydrolysable esters of a compound of the formula (I) or (I').

An in vivo hydrolysable ester of a compound of the formula (I) or (I') containing carboxy or hydroxy group is, for example, a pharmaceutically acceptable ester which is hydrolysed in the human or animal body to produce the parent acid or alcohol. Suitable pharmaceutically acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention.

An in vivo hydrolysable ester of a compound of the formula (I) or (I') containing a hydroxy group includes inorganic esters such as phosphate esters (including phosphoramidic cyclic esters) and α-acyloxyalkyl ethers and related compounds which as a result of the in vivo hydrolysis of the ester breakdown to give the parent hydroxy group/s. Examples of α-acyloxyalkyl ethers include acetoxymethoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4-position of the benzoyl ring.

Some compounds of the formula (I) or (I') may have chiral centres and/or geometric isomeric centres (E- and Z-isomers), and it is to be understood that the invention encompasses all such optical, diastereo-isomers and geometric isomers (and mixtures thereof) that possess CDK and/or FAK inhibitory activity.

The invention relates to any and all tautomeric forms of the compounds of the formula (I) or (I') that possess CDK and/or FAK inhibitory activity.

It is also to be understood that certain compounds of the formula (I) or (I') can exist in solvated as well as unsolvated forms such as, for example, hydrated forms. It is to be understood that the invention encompasses all such solvated forms which possess CDK and/or FAK inhibitory activity.

According to a further feature of the invention there is provided a pyrimidine derivative of the formula (I) or (I'):

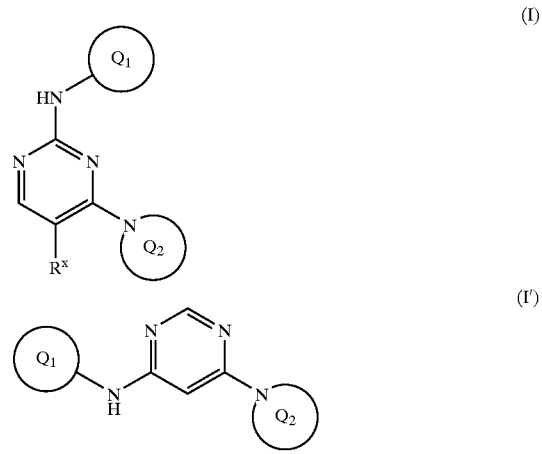

wherein:

$R^x$ is selected from hydrogen, halo, hydroxy, nitro, amino, $C_{1-3}$alkylamino, di-[$C_{1-3}$alkyl]amino, cyano, trifluoromethyl, trichloromethyl, $C_{1-3}$alkyl [optionally substituted by 1 or 2 substituents independently selected from halo, cyano, amino, $C_{1-3}$alkylamino, di-[$C_{1-3}$alkyl]amino, hydroxy and trifluoromethyl], $C_{3-5}$alkenyl [optionally substituted by up to three halo substituents, or by one trifluoromethyl substituent], $C_{3-5}$alkynyl, $C_{1-3}$alkoxy, —SH, —S—$C_{1-4}$alkyl, carboxy, $C_{1-3}$alkoxycarbonyl;

$Q_1$ is phenyl, and $Q_1$ bears on an available carbon atom not adjacent to the —NH— link one substituent of the formula (Ia'), and —NQ$_2$ (defined hereinbelow) may optionally bear on any available carbon atom farther substituents of the formula (Ia'):

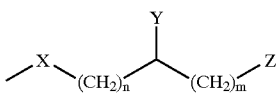

(Ia')

wherein:
X is CH$_2$, O, NH or S;
Y is H or as defined for Z;
Z is OH, SH, NH$_2$, C$_{1-4}$alkoxy, C$_{1-4}$alkylthio, —NH C$_{1-4}$alkyl, —N[C$_{1-4}$alkyl]$_2$, pyrrolidin-1-yl, piperidin-1-yl, piperazin-1-yl, morpholino or thiomorpholino;
n is 1, 2 or 3;
m is 1, 2 or 3;
and —NQ$_2$ is an unquaternised N-linked 8-, 9- or 10-membered bicyclic heterocyclic moiety containing one or two nitrogen heteroatoms and optionally containing a further one or two heteroatoms selected from nitrogen, oxygen and sulphur;

and Q$_1$ and —NQ$_2$ may optionally and independently bear on any available carbon atom up to four substituents independently selected from halo, hydroxy, thio, nitro, carboxy, cyano, C$_{2-4}$alkenyl [optionally substituted by up to three halo substituents, or by one trifluoromethyl substituent], C$_{2-4}$alkynyl, C$_{1-5}$alkanoyl, C$_{1-4}$alkoxycarbonyl, C$_{1-6}$alkyl, hydroxy-C$_{1-3}$alkyl, fluoro-C$_{1-4}$alkyl, amino-C$_{1-3}$alkyl, C$_{1-4}$alkylamino-C$_{1-3}$alkyl, di-[C$_{1-4}$alkyl]amino-C$_{1-3}$alkyl, cyano-C$_{1-4}$alkyl, C$_{2-4}$alkanoyloxy-C$_{1-4}$alkyl, C$_{1-4}$alkoxy-C$_{1-3}$alkyl, carboxy-C$_{1-4}$alkyl, C$_{1-4}$alkoxycarbonyl-C$_{1-4}$alkyl, carbamoyl-C$_{1-4}$alkyl, N-C$_{1-4}$alkylcarbamoyl-C$_{1-4}$alkyl, N,N-di-[C$_{1-4}$alkyl]-carbamoyl-C$_{1-4}$alkyl, pyrrolidin-1-yl-C$_{1-3}$alkyl, piperidin-1-yl-C$_{1-3}$alkyl, piperazin-1-yl-C$_{1-3}$alkyl, morpholino-C$_{1-3}$alkyl, thiomorpholino-C$_{1-3}$alkyl, piperazin-1-yl, morpholino, thiomorpholino, C$_{1-4}$alkoxy, cyano-C$_{1-4}$alkoxy, carbamoyl-C$_{1-4}$alkoxy, N-C$_{1-4}$alkylcarbamoyl-C$_{1-4}$alkoxy, N,N-di-[C$_{1-4}$alkyl]-carbamoyl-C$_{1-4}$alkoxy, 2-aminoethoxy, 2-C$_{1-4}$alkylaminoethoxy, 2-di-[C$_{1-4}$alkyl]aminoethoxy, C$_{1-4}$alkoxycarbonyl-C$_{1-4}$alkoxy, halo-C$_{1-4}$alkoxy, 2-hydroxyethoxy, C$_{2-4}$alkanoyloxy-C$_{2-4}$alkoxy, 2-C$_{1-4}$alkoxyethoxy, carboxy-C$_{1-4}$alkoxy, C$_{3-5}$alkenyloxy, C$_{3-5}$alkynyloxy, C$_{1-4}$alkylthio, C$_{1-4}$alkylsulphinyl, C$_{1-4}$alkylsulphonyl, ureido(H$_2$N—CO—NH—), C$_{1-4}$alkylNH—CO—NH—, di-[C$_{1-4}$alkyl]N—CO—NH—, C$_{1-4}$alkylNH—CO—N[C$_{1-4}$alkyl]-, di-[C$_{1-4}$alkyl]N—CO—N[C$_{1-4}$alkyl]-, carbamoyl, N-[C$_{1-4}$alkyl]carbamoyl, N,N-di-[C$_{1-4}$alkyl]carbamoyl, amino, C$_{1-4}$alkylamino, di-[C$_{1-4}$alkyl]amino, C$_{2-4}$alkanoylamino, and also independently, or in addition to, the above optional substituents, Q$_1$ and —NQ$_2$ may optionally and independently bear on any available carbon atom up to two further substituents independently selected from phenyl-C$_{1-4}$alkyl, phenyl-C$_{1-4}$alkoxy, phenyl, naphthyl, benzoyl and a 5- or 6-membered aromatic heterocycle (linked via a ring carbon atom and containing one to three heteroatoms independently selected from oxygen, sulphur and nitrogen); wherein said naphthyl, phenyl, benzoyl, 5- or 6-membered aromatic heterocyclic substituents and the phenyl group in said phenyl-C$_{1-4}$alkyl and phenyl-C$_{1-4}$alkoxy substituents may optionally bear one or two substituents independently selected from halo, C$_{1-4}$alkyl and C$_{1-4}$alkoxy;
or a pharmaceutically acceptable salt or in vivo hydrolysable ester thereof.

Particular preferred compounds of the invention comprise a pyrimidine derivative of the formula (I) or (I'), or pharmaceutically acceptable salt or in vivo hydrolysable ester thereof, wherein R$^x$, Q$_1$, —NQ$_2$, X, Y, Z, m and n have any of the meanings defined hereinbefore, or any of the following values:

(a) —NQ$_2$ is preferably indoline;
(b) —NQ$_2$ is more preferably indoline, piperazine, morpholine, indoline, 1,2,3,4-tetrahydronaphthalene, benzimidazole or indole;
(c) R$^x$ is preferably selected from hydrogen, halo, hydroxy, nitro, amino, C$_{1-3}$alkylamino, di-[C$_{1-3}$alkyl]amino, cyano, trifluoromethyl, C$_{1-3}$alkyl [optionally substituted by 1 or 2 substituents independently selected from halo, cyano, amino, C$_{1-3}$alkylamino, di-[C$_{1-3}$alkyl]amino, hydroxy and trifluoromethyl], C$_{3-5}$alkenyl [optionally substituted by up to three halo substituents, or by one trifluoromethyl substituent], C$_{3-5}$alkynyl, C$_{1-3}$alkoxy, —SH and —S—C$_{1-3}$alkyl;
(d) R$^x$ is more preferably selected from hydrogen, halo (especially chloro), nitro and C$_{1-3}$alkyl (especially methyl); R$^x$ is most preferably hydrogen or chloro;
(e) R$^x$ is particularly hydrogen, fluoro, chloro, bromo or methyl;
(f) Preferably in the substituent of formula (Ia') X is O, Y is OH and Z is —N[C$_{1-4}$alkyl]$_2$; preferably n is 1 and m is 1;
(g) Preferably in the substituent of formula (Ia) X is O, Y$^1$ is OH, Y$^2$ is H and Z is —N[C$_{1-4}$alkyl]$_2$; preferably n is 1 and m is 1;
(h) Most preferably the substituent of formula (Ia) or (Ia') is 3-dimethylamino-2-hydroxypropoxy;
(i) Preferably there is one substituent of formula (Ia) or (Ia'), i.e. preferably —NQ$_2$ does not bear a substituent of formula (Ia) or (Ia');
(j) The substituent of formula (Ia) or (Ia') in Q$_1$ must be in either the para- or meta-position relative to the —NH—, preferably in the para-position;
(k) Preferable further substituents for —NQ$_2$ include halo (especially bromo), C$_{1-5}$alkanoyl (especially acetyl) and C$_{1-4}$alkyl (especially methyl);
(l) Preferably the ring —NQ$_2$ not bearing the substituent of formula (Ia) or (Ia') is substituted by one or two further substituents, preferably halo (especially bromo), C$_{1-5}$alkanoyl (especially acetyl) or C$_{1-4}$alkyl (especially methyl);
(m) Preferably —NQ$_2$ is optionally substituted by halo, C$_{1-5}$alkanoyl or C$_{1-4}$alkyl; and if a heterocyclic moiety in —NQ$_2$ contains an —NH— moiety preferably that nitrogen is unsubstituted or substituted by C$_{1-4}$alkoxycarbonyl;
(n) —NQ$_2$ is indoline, 4-t-butyloxycarbonylpiperazine, piperazine, morpholine, 2-methylindoline, 5-bromoindoline, 5-acetylindoline, 2,3-dimethylindoline, 1,2,3,4-tetrahydronaphthalene, benzimidazole or indole;
(o) Preferably if a heterocyclic moiety in —NQ$_2$ contains an —NH— moiety that nitrogen is unsubstituted or substituted by C$_{1-6}$alkoxycarbonyl;
(p) In one aspect of the invention preferably the compound is of formula (I); and
(q) In another aspect of the invention, preferably the compound is of formula (I').

A preferred compound of the invention is a pyrimidine derivative of the formula (I), or pharmaceutically acceptable salt or in vivo hydrolysable ester thereof, wherein:

$Q_1$ is phenyl and —$NQ_2$ is indoline;

$R^x$ is hydrogen or chloro (especially hydrogen);

$Q_1$ bears one substituent of formula (Ia) or (Ia') (especially 3-dimethylamino-2-hydroxypropoxy), preferably in the para-position;

—$NQ_2$ bears one or two substituents independently selected from halo (especially bromo), $C_{1-5}$alkanoyl (especially acetyl) and $C_{1-4}$alkyl (especially methyl).

A more preferred compound of the invention is a pyrimidine derivative of the formula (I) or (I'), or pharmaceutically acceptable salt or in vivo hydrolysable ester thereof, wherein:

$Q_1$ is phenyl and —$NQ_2$ is indoline, piperazine (optionally substituted on the 4-nitrogen by t-butoxycarbonyl), morpholine, indoline, 1,2,3,4-tetrahydronaphthalene, benzimidazole or indole;

$R^x$ is hydrogen, fluoro, chloro, bromo or methyl;

$Q_1$ bears one substituent in the para-position of formula (Ia) or (Ia') which is 3-dimethylamino-2-hydroxypropoxy;

—$NQ_2$ bears one or two substituents on carbon independently selected from bromo, acetyl and methyl.

A specific preferred compound of the invention is the pyrimidine derivative of the formula (I), being Example 5 (described hereinafter); or pharmaceutically acceptable salt or in vivo hydrolysable ester thereof.

In a further aspect of the invention preferred compounds of the invention include any one of the Examples or pharmaceutically acceptable salt or in vivo hydrolysable ester thereof.

Preferred aspects of the invention are those which relate to the compound or a pharmaceutically acceptable salt thereof.

A pyrimidine derivative of the formula (I) or (I'), or a pharmaceutically acceptable salt or an in vivo hydrolysable ester thereof, may be prepared by any process known to be applicable to the preparation of chemically-related compounds. Such processes, when used to prepare a pyrimidine derivative of the formula (I) or (I'), or a pharmaceutically acceptable salt or an in vivo hydrolysable ester thereof, are provided as a further feature of the invention and are illustrated by the following representative examples in which (unless otherwise stated) $Q_1$, —$NQ_2$, $R^x$, X, $Y^1$, $Y^2$, Z, m and n have any of the meanings defined hereinbefore for a pyrimidine derivative of the formula (I) or (I'), and unless another substituent is drawn on ring $Q_1$ or —$NQ_2$ the ring may bear any of the substituents described hereinbefore (optionally protected as necessary). Where a substituent is drawn on ring $Q_1$, this includes (unless stated otherwise) the possibilities (as appropriate) of the substituent being on ring —$NQ_2$ in addition to, or instead of, the substituent being on ring $Q_1$. Where X is defined in this section as —NH— it is to be understood that this also includes the possibility of X as —$NR^y$—. Necessary starting materials may be obtained by standard procedures of organic chemistry (see, for example, Advanced Organic Chemistry (Wiley-Interscience), Jerry March—also useful for general guidance on reaction conditions and reagents). The preparation of such starting materials is described within the accompanying non-limiting processes and Examples. Alternatively necessary starting materials are obtainable by analogous procedures to those illustrated which are within the ordinary skill of an organic chemist.

2,4-Pyrimidines: Processes

Thus, as a further feature of the invention there are provided the following processes for preparing compounds of formula (I) which comprises of:

Process a)

reacting a pyrimidine of formula (II):

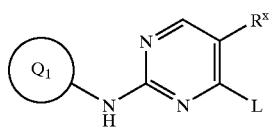

(II)

wherein L is a displaceable group as defined below, with a compound of formula (III):

(III)

Process b)

reaction of a pyrimidine of formula (IV):

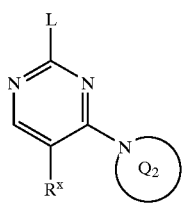

(IV)

wherein L is a displaceable group as defined below, with a compound of formula (V):

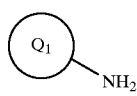

(V)

Process c)

for compounds of formula (I) where n is 1, 2 or 3, m=1 $Y^2$ is H and $Y^1$ is OH, $NH_2$ or SH, by reaction of a three-membered heteroalkyl ring containing compound of formula (VI):

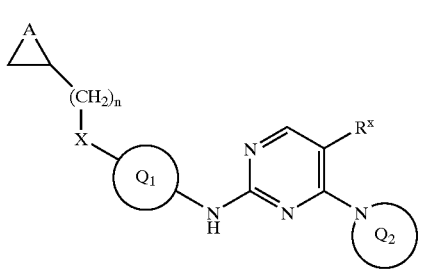

(VI)

wherein A is O, S or NH;

with a nucleophile of formula (VII):

Z—D (VII)

wherein D is H or a suitable counter-ion;

Process d)

for compounds of formula (I) where X is oxygen, by reaction of an alcohol of formula (VIII):

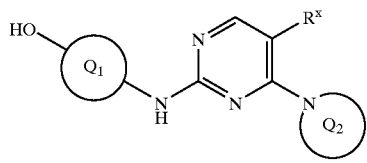
(VIII)

with an alcohol of formula (IX):

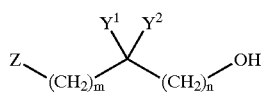
(IX)

Process e)

for compounds of formula (I) wherein X is —CH$_2$—, —O—, —NH— or —S—, Y$^1$ is OH, Y$^2$ is H and m is 2 or 3; reaction of a compound of formula (X):

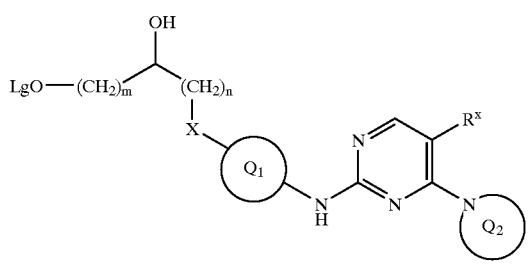
(X)

wherein LgO is a leaving group as defined below; with a nucleophile of formula (VII);

Process f)

for compounds of formula (I) wherein X is —CH$_2$—, —O—, —NH— or —S—, Y$^1$ is H, Y$^2$ is H, n is 1, 2 or 3 and m is 1, 2 or 3; reaction of a compound of formula (XI):

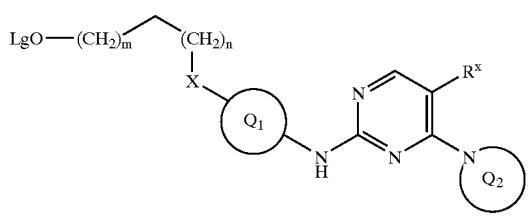
(XI)

wherein LgO is a leaving group as defined below; with a nucleophile of formula (VII);

Process g)

for compounds of formula (I) wherein X is —O—, —NH— or —S—, Y$^1$ is H, Y$^2$ is H, n is 1, 2 or 3 and m is 1, 2 or 3; reaction of a compound of formula (XII):

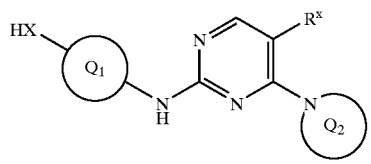
(XII)

with a compound of formula (XIII)

$$Z\text{—}(CH_2)_m\text{—}\overset{}{\phantom{C}}\text{—}(CH_2)_n\text{—}L$$
(XIII)

wherein L is a displaceable group as defined below;

Process h)

for compounds of formula (I) in which Z is HS—, by conversion of a thioacetate group in a corresponding compound;

and thereafter if necessary:
i) converting a compound of the formula (I) into another compound of the formula (I);
ii) removing any protecting groups;
iii) forming a pharmaceutically acceptable salt or in vivo hydrolysable ester.

L is a displaceable group, suitable values for L are for example, a halo or sulphonyloxy group, for example a chloro, bromo, methanesulphonyloxy or toluene-4-sulphonyloxy group. Alternative suitable groups for L include halo, mesyl, methylthio and methylsulphinyl.

D is hydrogen or a counter-ion. When D is a counter-ion, suitable values for D include sodium and potassium.

LgO is a leaving group. Suitable values for LgO include mesylate and tosylate.

Specific reaction conditions for the above reactions are as follows:

Process a)

Pyrimidines of formula (II) and compounds of formula (III) may be reacted together
i) optionally in the presence of a suitable acid, for example an inorganic acid such as hydrochloric acid or sulphuric acid, or an organic acid such as acetic acid or formic acid. The reaction is preferably carried out in a suitable inert solvent or diluent, for example dichloromethane (DCM), acetonitrile, butanol, tetramethylene sulphone, tetrahydrofuran, 1,2-dimethoxyethane, N,N-dimethylformamide, N,N-dimethylacetamide or N-methylpyrrolidin-2-one, and at a temperature in the range, for example, 0° to 150° C., conveniently at or near reflux temperature; or
ii) under standard Buchwald conditions (for example see *J. Am. Chem. Soc.*, 118, 7215; *J. Am. Chem. Soc.*, 119, 8451; *J. Org. Chem.*, 62, 1568 and 6066) for example in the presence of palladium acetate, in a suitable solvent for example an aromatic solvent such as toluene, benzene or xylene, with a suitable base for example an inorganic base such as caesium carbonate or an organic base such as potassium-t-butoxide, in the presence of a suitable ligand such as 2,2'-bis(diphenylphosphino)-1,1'-binaphthyl and at a temperature in the range of 25 to 80° C.

Pyrimidines of the formula (II) may be prepared according to the following scheme:

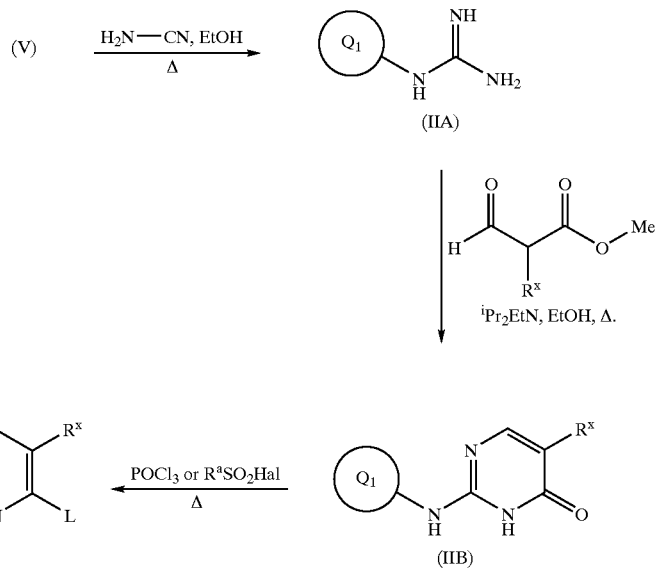

wherein $R^a$ is an optionally substituted alkyl or aryl group and L is a displaceable group as defined above. Preferably $R^a$ is methyl, ethyl or p-tolyl.

Compounds of formula (V) and (III) are commercially available or are prepared by processes known in the art.

Process b)

Pyrimidines of formula (IV) and compounds of formula (V) may be reacted together in the presence of a suitable solvent for example a ketone such as acetone or an alcohol such as ethanol or butanol or an aromatic hydrocarbon such as toluene or N-methyl pyrrolidine, or a solvent such as tetramethylene sulphone, optionally in the presence of a suitable acid (such as those defined for process a) above or a Lewis acid) or base (such as Hunig's base or calcium carbonate) and at a temperature in the range of 0° C. to reflux, preferably reflux.

Pyrimidines of the formula (IV) may be prepared according to the following scheme:

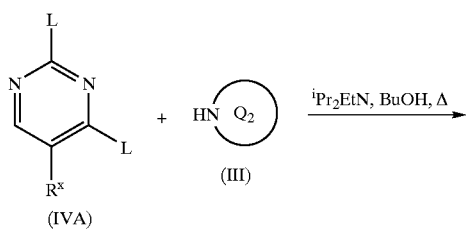

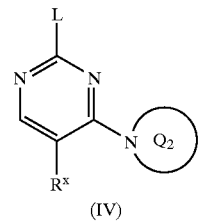

The compounds of formula (IVA), (III) and (V) are commercially available or are prepared by processes known in the art. For example, pyrimidines of the formula (IVA) may be prepared by, for example, reacting a compound of formula (IVA) in which L is —OH (i.e. a uracil), with $POCl_3$ to give a compound of formula (IVA) in which L is —Cl.

Process c)

Three-membered heteroalkyl ring containing compounds of formula (VI) and nucleophiles of formula (VII) are reacted together at a temperature in the range of 20° to 100° C., preferably 20° to 50° C., optionally in the presence of a suitable solvent, for example N,N-dimethylformamide, dimethyl sulfoxide or tetrahydrofuran.

Compounds of formula (VI) may be prepared according to the following schemes:

Scheme I)

For compounds of formula (VI) where A is O, and X is not carbon:

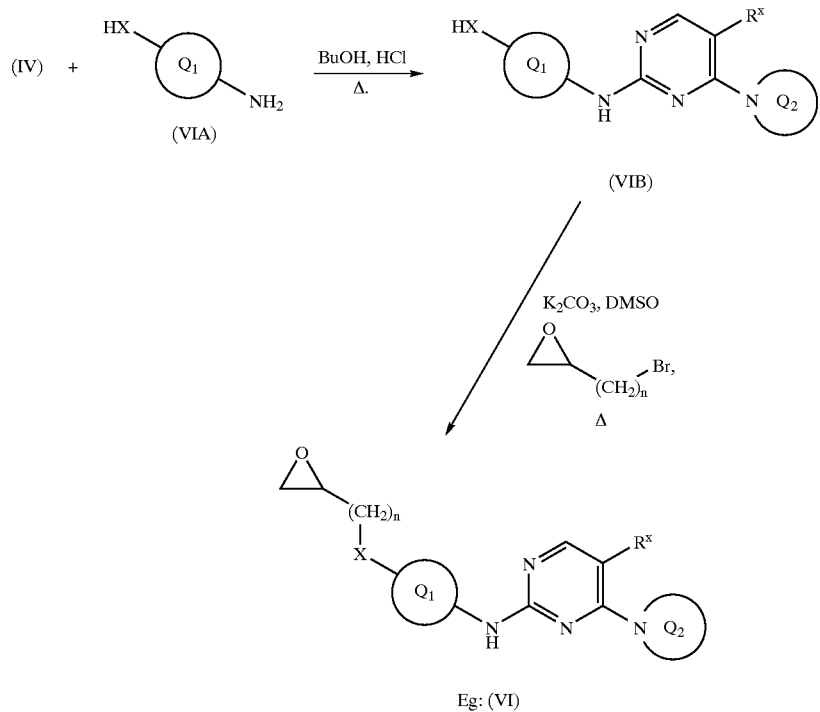

The conversion of (VIB) to (VI) may also be achieved by reaction with Br—(CH$_2$)$_n$—CHO, or an equivalent ester, in DMF and the presence of a base, followed by reaction with a sulphur ylide such as (Me$_2$SOCH$_2$) in an inert solvent such as THF (see scheme V).

Scheme II)

For compounds of formula (VI) where A is NH, and X is not carbon:

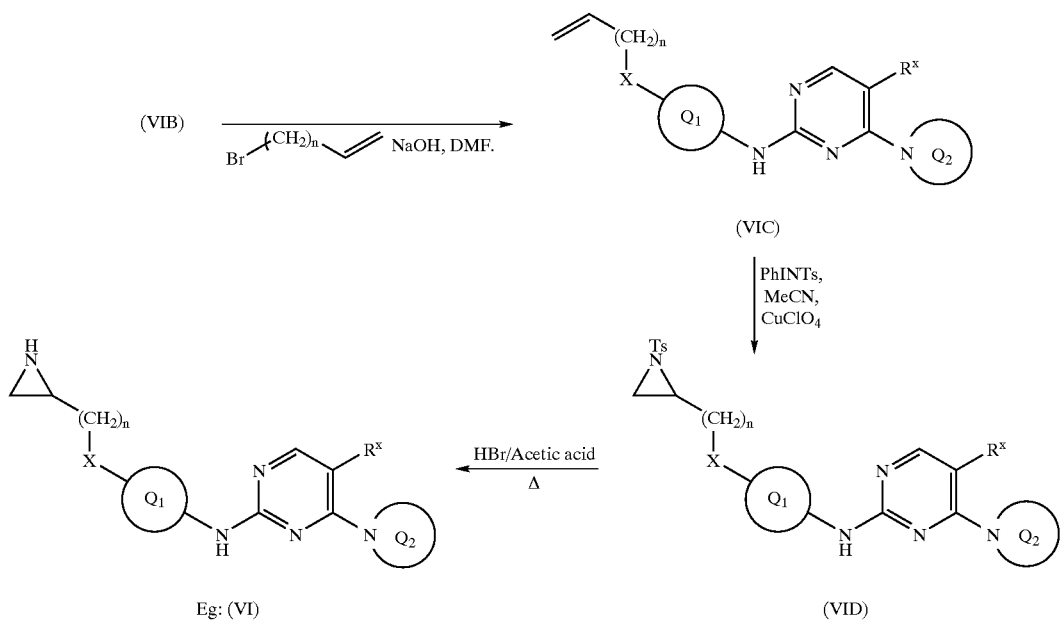

(for PhINTs see, for example, Tet. Let., 1997, 38 (39), 6897–6900; compounds of formula (VIC) may also be oxidised to the epoxide using conditions similar to that in Scheme IV) below);

Scheme III)

For compounds of formula (VI) where A is S, and X is not carbon:

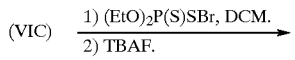

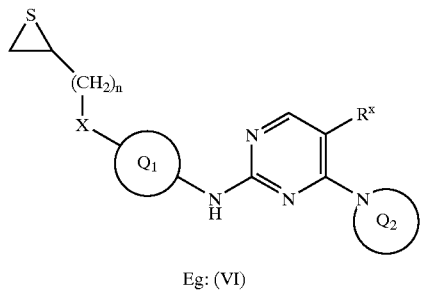

Eg: (VI)

(for example see Synlett, 1994, 267–268);

Scheme V)

For compounds of formula (VI) wherein X is CH$_2$, O, NH or S; Y$^1$ is OH; Y$^2$ is H; n is 1, 2 or 3 and m is 1:

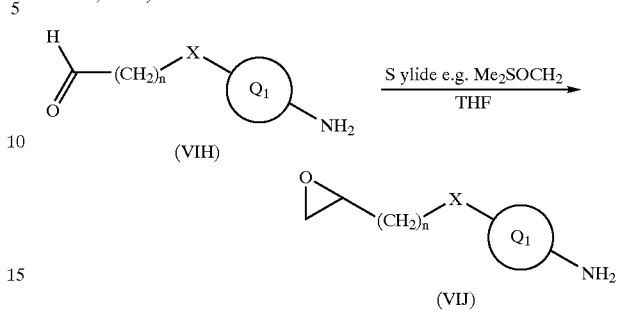

(VIJ) is reacted with (IV) (in the manner of Scheme I) to give (VI).

An equivalent ester of (VIH) may also be used. See also Russ. Chem. Rev. 47, 975–990, 1978.

Scheme IV)

For compounds of formula (VI) where X is carbon

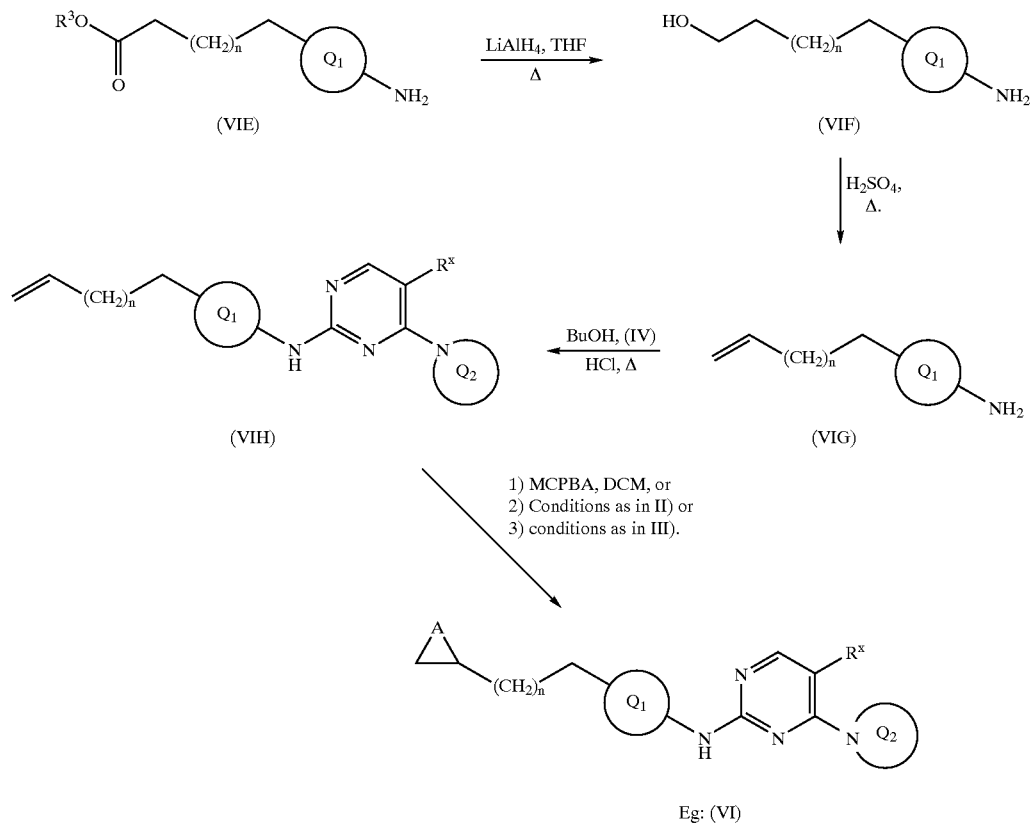

wherein R$^3$ together with the —COO— group to which it is attached forms an ester moiety, for example a methyl ester or an ethyl ester.

Compounds of formula (VIH), (VII) and (VIA) and (VIE) are commercially available or are prepared by processes known in the art.

Process d)

Alcohols (eg phenols) of formula (VIII) and (IX) can be reacted together under standard Mitsunobu conditions. For example in the presence of diethyl azodicarboxylate and triphenyl phosphine, in a suitable solvent such as dichloromethane, toluene or tetrahydrofuran, and at a temperature in the range of 0° to 80° C., preferably in the range of 20° to 60° C. Alternatively, alcohols of formula (VIII) may be alkylated with a suitable compound of formula (IX) in which the terminal hydroxy group has been replaced by a suitable leaving group.

Alcohols of formula (VIII) are made according to the Scheme I) above for the synthesis of intermediate (VIB) (where X is oxygen).

Alcohols of formula (IX) are commercially available or are made by processes known in the art.

In a process analogous to process d), compounds in which X is —S— may be prepared by reaction of a compound of formula (VIII) in which the hydroxy group is —SH, with a compound of formula (IX) in which the hydroxy group is a leaving group such as mesylate or tosylate.

Process e)

Compounds of formula (X) wherein X is —CH$_2$—, —O—, —NH— or —S—; $Y^1$ is OH; $Y^2$ is H and m is 2 or 3 and nucleophiles of formula (VII) are reacted together at a temperature in the range of 20° to 100° C., preferably 20° to 50° C., optionally in the presence of a suitable solvent, for example N,N-dimethylformamide, dimethyl sulphoxide or tetrahydrofuran, and optionally in the presence of a suitable base, such as potassium carbonate.

Compounds of formula (X) are prepared according to the following scheme (m is 2 or 3):

Process f)

Compounds of formula (XI) and nucleophiles of formula (VII) are reacted together as described for process e) above.

Compounds of formula (XI) are prepared in an analogous manner to step 2) in the final step of the process for preparing compounds of formula (X) above. The necessary primary alcohol starting materials are commercially available or are prepared by processes known in the art.

Process g)

Compounds of formula (XII) and (XIII) are reacted in an inert solvent such as DMF in the presence of a base such as potassium carbonate.

Compounds of formula (XII) are of the same generic formula as compounds of formula (VIB) described herein and are prepared as described for those compounds (see Scheme I). Compounds of formula (XIII) are commercially available or are prepared by processes known in the art.

Process h)

For the compounds of formula (I) in which Z is SH, the conversion of a thioacetate group in a corresponding compound is carried out as described herein for the conversion of compounds of formula (IJ) into (IK).

Suitable starting materials containing a thioacetate group are prepared from corresponding compounds containing a leaving group such as mesylate or tosylate (prepared using standard conditions from the corresponding hydroxy compound) using thiol acetic acid as described herein for the conversion of compounds of formula (IG) into (IJ).

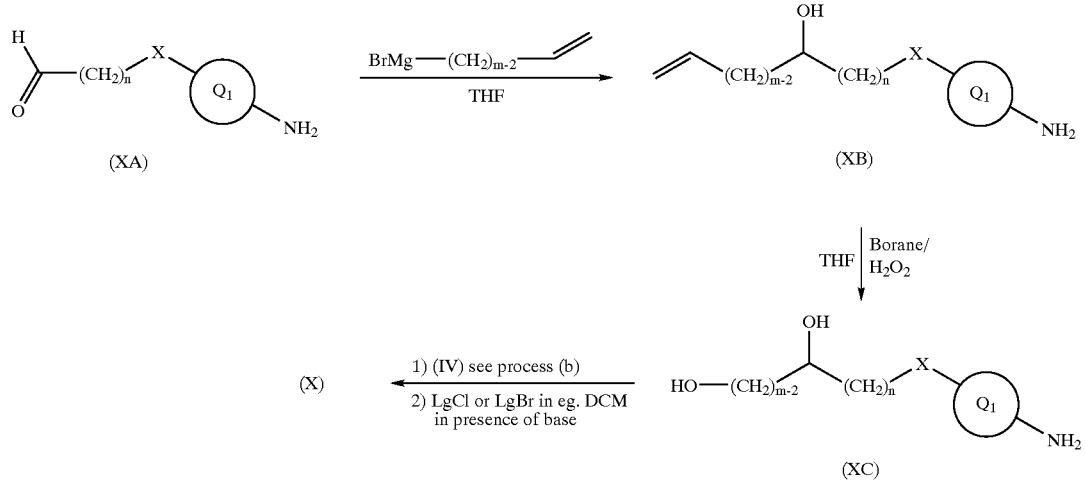

The order of steps 1) and 2) in the final step may be reversed. A suitable base for step 2) is triethylamine.

Compounds of formula (XA) and (VII) are commercially available or are prepared by processes known in the art. For example, compounds of formula (XA) in which X is —NH—, —O— or —S— may be prepared by reaction of a compound of formula (VIA) with a suitable haloaldehyde or equivalent ester under standard conditions for such reactions.

Examples of conversions of a compound of formula (I) into another compound of formula (I) are:
Conversion i) of one side chain of formula (Ia) or (Ia') into another side chain of formula (Ia) or (Ia'), for example:
Conversion I) for compounds of formula (I) where $Y^1$ is H and $Y^1$ is NH$_2$ (depicted below using ammonia), C$_{1-4}$alkoxy, C$_{1-4}$alkylthio, —NH C$_{1-4}$alkyl, —N[C$_{1-4}$alkyl]$_2$, pyrrolidin-1-yl, piperidin-1-yl, piperazin-1-yl, morpholino or thiomorpholino;

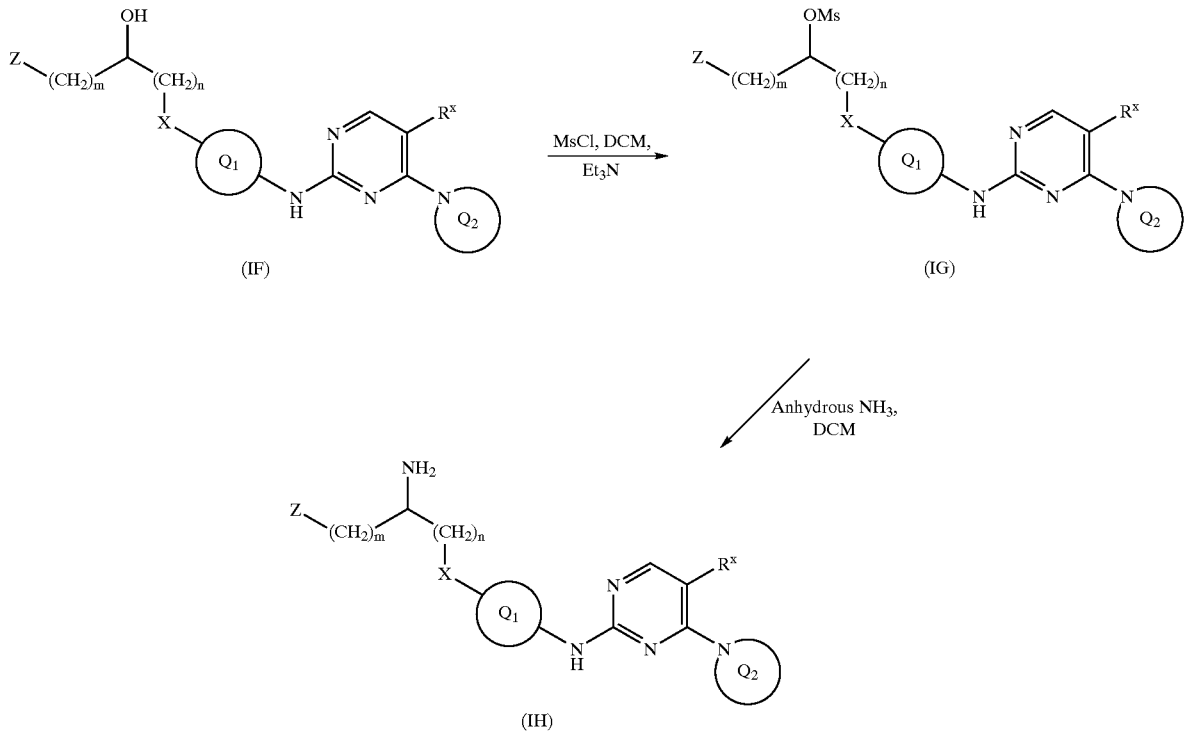
or
Conversion II) for compounds of formula (I) where $Y^2$ is H and $Y^1$ is S:
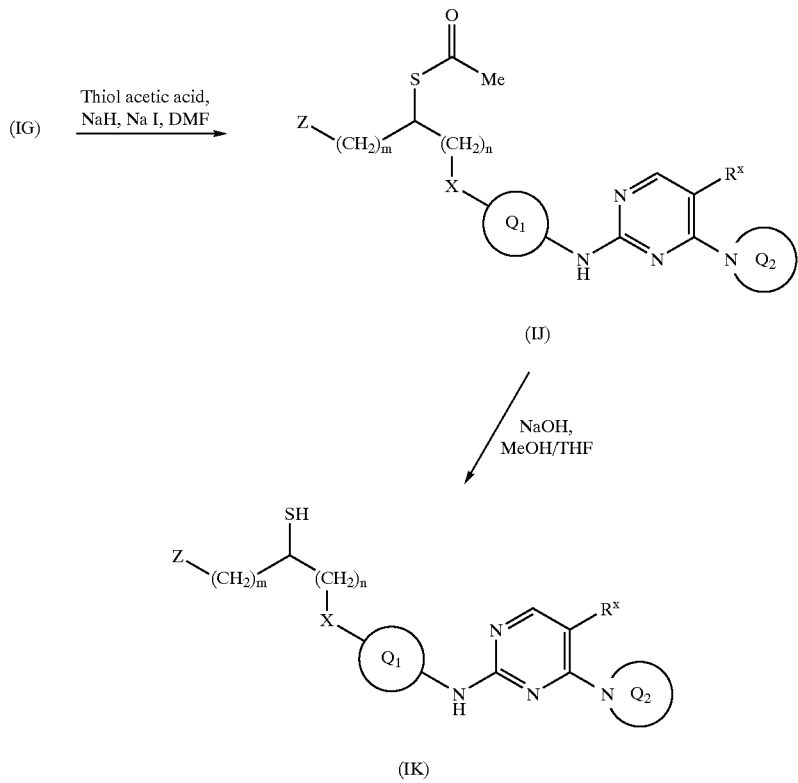

Conversion III) for compounds of formula (I) where $Y^1$ is H and $Y^2$ is H:

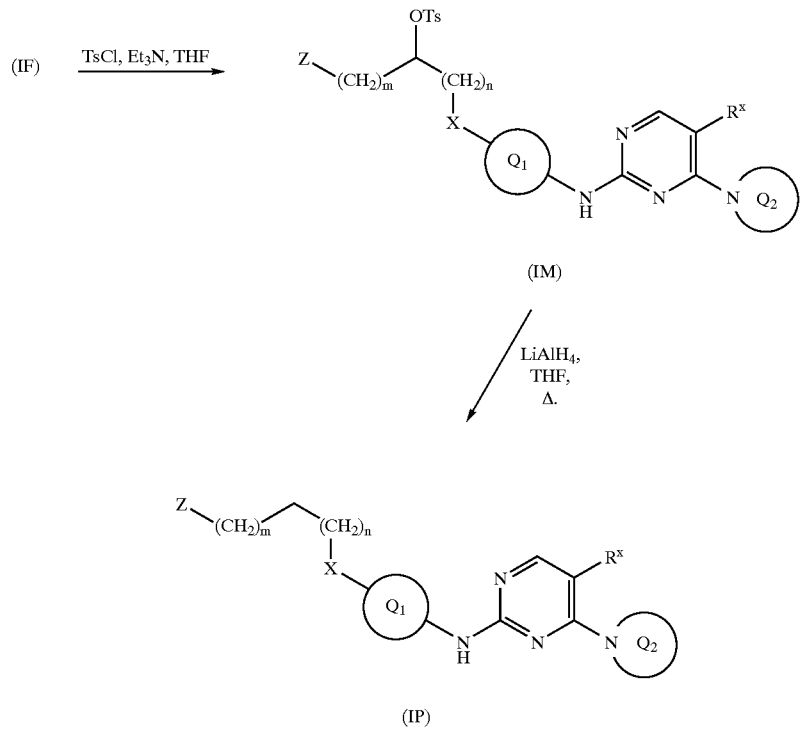

Conversion ii) of one value of $R^x$ into another value of $R^x$ using standard techniques, for example, conversion of $R^x$ as hydroxy into $C_{1-3}$alkoxy.

The skilled reader will appreciate that the manipulation of the side chain (Ia) or (Ia') described in processes c) and d) above may also be performed on intermediates for example to make intermediates of formula (II), (IIA), (IIB), or (V). For example:

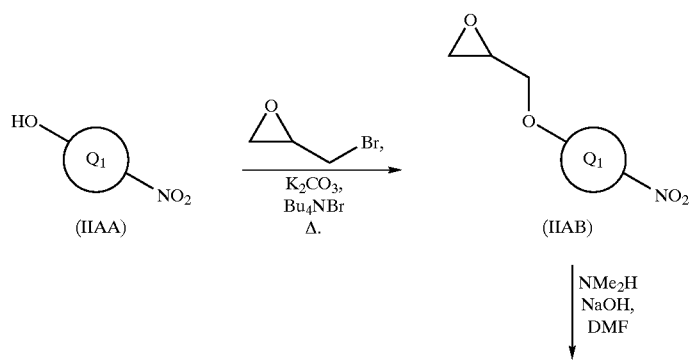

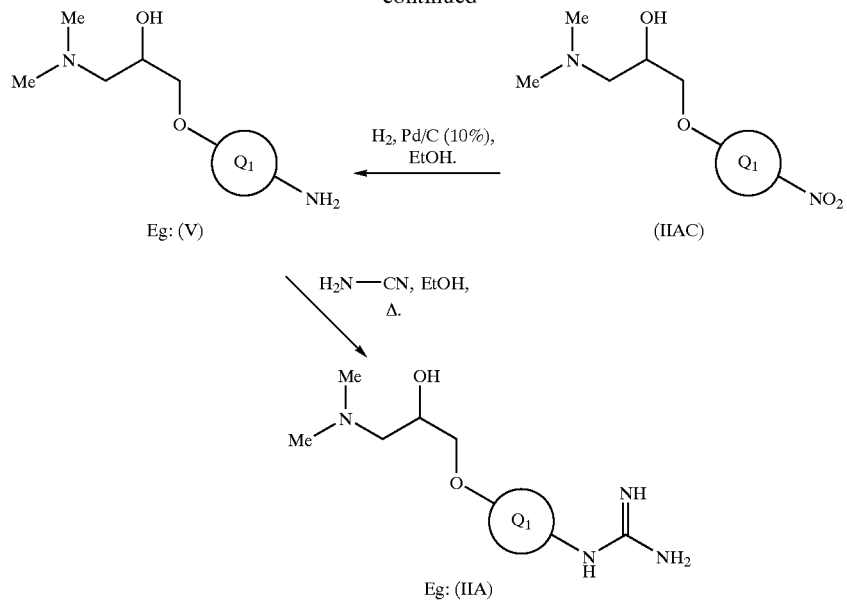

4,6-Pyrimidines: Processes

Thus, as a further feature of the invention there are provided the following processes for preparing compounds of formula (I') which comprises of:

Process a')

reacting a pyrimidine of formula (II'):

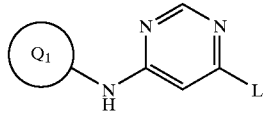
(II')

wherein L is a displaceable group as defined below, with a compound of formula (III'):

(III')

Process b')

reaction of a pyrimidine of formula (IV'):

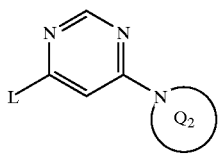
(IV')

wherein L is a displaceable group as defined below, with a compound of formula (V'):

(V')

Process c')

for compounds of formula (I') where n is 1, 2 or 3, m=1, $Y^2$ is H and $Y^1$ is OH, $NH_2$ or SH, reaction of a 3-membered heteroalkyl ring of formula (VI'):

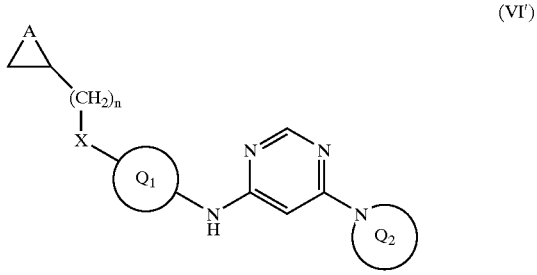
(VI')

wherein A is O, S or NH;

with a nucleophile of formula (VII'):

Z—D   (VII')

wherein D is H or a suitable counter-ion;

Process d')

for compounds of formula (I') where X is oxygen, by reaction of an alcohol of formula (VIII'):

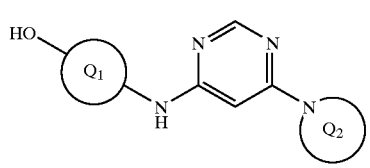

(VIII')

with an alcohol of formula (IX'):

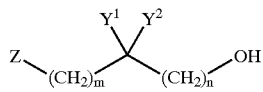

(IX')

Process e')

for compounds of formula (I') wherein X is —CH$_2$—, —O—, —NH— or —S—, Y$^1$ is OH, Y$^2$ is H and m is 2 or 3; reaction of a compound of formula (X'):

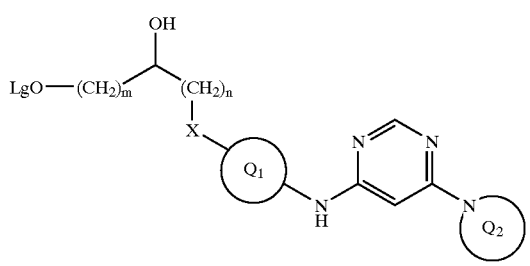

(X')

wherein LgO is a leaving group as defined below; with a nucleophile of formula (VII');

Process f)

for compounds of formula (I') wherein X is —CH$_2$—, —O—, —NH— or —S—;
Y$^1$ is H; Y$^2$ is H; n is 1, 2 or 3 and m is 1, 2 or 3; reaction of a compound of formula (XI'):

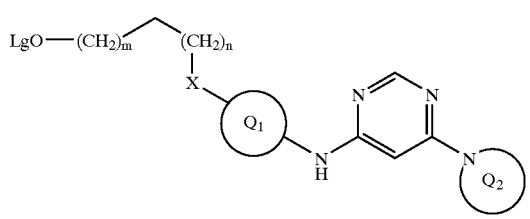

(XI')

wherein LgO is a leaving group as defined below; with a nucleophile of formula (VII');

Process g')

for compounds of formula (I') wherein X is —O—, —NH— or —S—; Y$^1$ is H;
Y$^2$ is H; n is 1, 2 or 3 and m is 1, 2 or 3; reaction of a compound of formula (XII'):

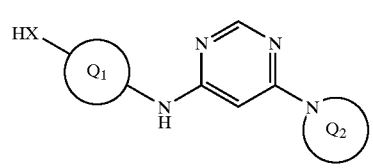

(XII')

with a compound of formula (XIII')

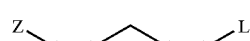

(XIII')

wherein L is a displaceable group as defined below;
Process h')

for compounds of formula (I') in which Z is HS—, by conversion of a thioacetate group in a corresponding compound;

and thereafter if necessary:
  i) converting a compound of the formula (I') into another compound of the formula (I');
  ii) removing any protecting groups;
  iii) forming a pharmaceutically acceptable salt or in vivo hydrolysable ester.

Unless stated otherwise, the value of variables (such as L and D) in this 4,6-pyrimidines process section are as described in the above 2,4-pyrimidines process section.

Specific reaction conditions for the above 4,6-pyrimidines process reactions are as follows:

Process a')

Pyrimidines of formula (II') and compounds of formula (III') may be reacted together s described in the above 2,4-pyrimidines process a).

Pyrimidines of the formula (II') may be prepared according to the following scheme:

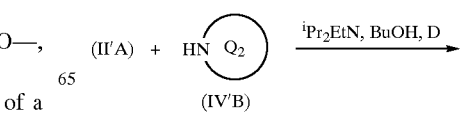

Compounds of formula (III') are commercially available or are prepared by processes known in the art.

Process b')

Pyrimidines of formula (IV') and compounds of formula (V') may be reacted together as described in the above 2,4-pyrimidines process b).

Pyrimidines of formula (IV') are prepared according to the following scheme:

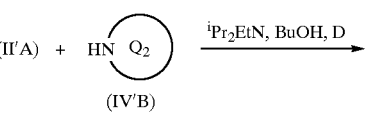

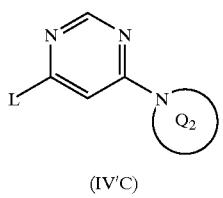

(IV'C)

wherein L is a displaceable group as defined above.

The compounds of formula (V') are commercially available or are prepared by processes known in the art.

Process c')

Three membered heteroalkyl rings of formula (VI') and nucleophiles of formula (VII') are reacted together as described in the above 2,4-pyrimidines process c).

Compounds formula (VI') may be prepared according to schemes analogous to Schemes I) to IV) as described above in the 2,4-pyrimidines process section (but using 4,6-pyrimidine compounds in place of the 2,4-pyrimidines shown in the above mentioned schemes).

Compounds of formula (VII') and necessary intermediates are commercially available or are prepared by processes known in the art (by analogy with the 2,4-pyrimidines process section c) described above).

Process d')

Alcohols of formula (VIII') and (IX') can be reacted together under standard Mitsunobu conditions as described in the above 2,4-pyrimidines process d).

Alcohols of formula (VIII') are made by analogy with the 2,4-pyrimidines process section d) described above.

Alcohols of formula (IX') are commercially available or are made by processes known in the art.

Process e')

Compounds of formula (X') and (VII') can be reacted together under standard conditions as described in the above 2,4-pyrimidines process e).

Compounds of formula (X') are made by analogy with the 2,4-pyrimidines process section d) described above.

Compounds of formula (VII') are commercially available or are made by processes known in the art.

Process f)

Compounds of formula (XI') and (VII') can be reacted together under standard conditions as described in the above 2,4-pyrimidines process f).

Compounds of formula (XI') are made by analogy with the 2,4-pyrimidines process section d) described above.

Process g')

Compounds of formula (XII') and (XIII') can be reacted together under standard conditions as described in the above 2,4-pyrimidines process g).

Compounds of formula (X'II) are made by analogy with the 2,4-pyrimidines process section d) described above.

Compounds of formula (XIII') are commercially available or are made by processes known in the art.

Process h')

Conversion of the thioacetate can be achieved standard conditions as described in the above 2,4-pyrimidines process h).

Examples of conversions of a compound of formula (I') into another compound of formula (I') are analogous to those conversions I) to III) described above for 2,4-pyrimidines of formula (I), for example, the conversion of one side chain of formula (Ia) or (Ia') into another side chain of formula (Ia) or (Ia') (but using 4,6-pyrimidine compounds in place of the 2,4-pyrimidines shown in the above mentioned conversions).

As for the conversions described above for 2,4-pyrimidines of formula (I), the skilled reader will appreciate that the manipulation of the side chain (Ia) or (Ia') described may also be performed on intermediates (by analogy with the 2,4-pyrimidines process section d) described above).

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halo group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

Many of the intermediates defined herein are novel, for example, those of the formula II and IV and these are provided as a further feature of the invention.

ASSAYS

As stated hereinbefore the pyrimidine derivative defined in the present invention possesses anti-cell-proliferation activity such as anti-cancer activity which is believed to arise from the CDK and/or FAK inhibitory activity of the compound. These properties may be assessed, for example, using the procedure set out below:

CDK4 Inhibition Assay

The following abbreviations have been used:

HEPES is N-(2-Hydroxyethyl)piperazine-N'-(2-ethanesulfonic acid)

DTT is Dithiothretiol

PMSF is Phenylmethylsulfonyl fluoride

The compounds were tested in an in vitro kinase assay in 96 well format using Scintillation Proximity Assay (SPA—obtained from Amersham) for measuring incorporation of [γ-33-P]-Adenosine Triphosphate into a test substrate (GST-Retinoblastoma). In each well was placed the compound to be tested (diluted in DMSO and water to correct concentrations) and in control wells either p16 as an inhibitor control or DMSO as a positive control.

Approximately 0.5 μl of CDK4/Cyclin D1 partially-purified enzyme (amount dependent on enzyme activity) diluted in 25 μl incubation buffer was added to each well then 20 μl of GST-Rb/ATP/ATP33 mixture (containing 0.5 μg GST-Rb and 0.2 μM ATP and 0.14 μCi [γ-33-P]-Adenosine Triphosphate), and the resulting mixture shaken gently, then incubated at room temperature for 60 minutes. To each well was then added 150 μL stop solution containing (0.8 mg/well of Protein A-PVT SPA bead (Amersham)), 20 pM/well of Anti-Glutathione Transferase, Rabbit IgG (obtained from Molecular Probes), 61 mM EDTA and 50 mM HEPES pH 7.5 containing 0.05% sodium azide.

The plates were sealed with Topseal-S plate sealers, left for two hours then spun at 2500 rpm, 1124×g., for 5 minutes. The plates were read on a Topcount for 30 seconds per well.

The incubation buffer used to dilute the enzyme and substrate mixes contained 50 mM HEPES pH7.5, 10 mM $MnCl_2$, 1 mM DTT, 100 μM Sodium vanadate, 100 μM NaF, 10 mM Sodium Glycerophosphate, BSA (1 mg/ml final).

As a control, another known inhibitor of CDK4 may be used in place of p16.

Test Substrate

In this assay only part of the retinoblastoma (Science Mar. 13, 1987; 235 (4794): 1394–1399; Lee W. H., Bookstein R., Hong F., Young L. J., Shew J. Y., Lee E. Y.) was used, fused to a GST tag. PCR of retinoblastoma amino acids 379–928 (obtained from retinoblastoma plasmid ATCC pLRbRNL) was performed, and the sequence cloned into pGEX 2T fusion vector (Smith D. B. and Johnson, K. S. Gene 67, 31 (1988); which contained a tac promoter for inducible expression, internal lac $I^q$ gene for use in any E. Coli host, and a coding region for thrombin cleavage—obtained from Pharmacia Biotech) which was used to amplify amino acids 792–928. This sequence was again cloned into pGEX 2T.

The retinoblastoma 792–928 sequence so obtained was expressed in E. Coli (BL21 (DE3) pLysS cells ) using standard inducible expression techniques, and purified as follows.

E. coli paste was resuspended in 10 ml/g of NETN buffer (50 mM Tris pH 7.5, 120 mM NaCl, 1 mM EDTA, 0.5%v/v NP-40, 1 mM PMSF, 1 μg/ml leupeptin, 1 μg/ml aprotinin and 1 μg/ml pepstatin) and sonicated for 2×45 seconds per 100 ml homogenate. After centrifugation, the supernatant was loaded onto a 10 ml glutathione Sepharose column (Pharmacia Biotech, Herts, UK), and washed with NETN buffer. After washing with kinase buffer (50 mM HEPES pH 7.5, 10 mM MgCl2, 1 mM DTT, imM PMSF, 1 μg/ml leupeptin, 1 μg/ml aprotinin and 1 μg/ml pepstatin) the protein was eluted with 50 mM reduced glutathione in kinase buffer. Fractions containing GST-Rb(792–927) were pooled and dialysed overnight against kinase buffer. The final product was analysed by Sodium Dodeca Sulfate (SDS) PAGE (Polyacrylamide gel) using 8–16% Tris-Glycine gels (Novex, San Diego, USA).

CDK4 and Cyclin D1

CDK4 and Cyclin D1 were cloned from RNA from MCF-7 cell line (obtained from ATCC number:HTB22, breast adenocarcinoma line) as follows. The RNA was prepared from MCF-7 cells, then reverse transcribed using oligo dT primers. PCR was used to amplify the complete coding sequence of each gene [CDK4 amino acids 1–303; Ref. Cell Oct. 16, 1992; 71(2): 323–334; Matsushime H., Ewen M. E., Stron D. K., Kato J. Y., Hanks S. K., Roussel M. F., Sherr C. J. and Cyclin D1 amino acids 1–296; Ref. Cold Spring Harb. Symp. Quant. Biol., 1991; 56:93–97; Arnold A., Motokura T., Bloom T., Kronenburg, Ruderman J., Juppner H., Kim H. G.].

After sequencing the PCR products were cloned using standard techniques into the insect expression vector pVL1393 (obtained from Invitrogen 1995 catalogue number: V1392-20). The PCR products were then dually expressed [using a standard virus Baculogold co-infection technique] into the insect SF21 cell system (*Spodoptera Frugiperda* cells derived from ovarian tissue of the Fall Army Worm—Commercially available).

The following Example provides details of the production of Cyclin D1/CDK4 in SF21 cells (in TC100+10% FBS (TCS)+0.2% Pluronic) having dual infection MOI 3 for each virus of Cyclin D1 & CDK4.

Example Production of Cyclin D1/CDK4

SF21 cells grown in a roller bottle culture to $2.33 \times 10^6$ cells/ml were used to inoculate 10×500 ml roller bottles at 0.2×10E6 cells/ml. The roller bottles were incubated on a roller rig at 28° C.

After 3 days (72 hrs.) the cells were counted, and the average from 2 bottles found to be 1.86×10E6 cells/ml.

(99% viable). The cultures were then infected with the dual viruses at an MOI 3 for each virus.

10×500 ml were infected with JS303 Cyclin D1 virus titre—9×10E7 pfu/ml. JS304 CDK4 virus titre—1×10E8 pfu/ml.

$$\text{Cyclin } D1 \; \frac{1.86 \times 10E6 \times 500 \times 3}{0.9 \times 10^8} =$$

31 ml of virus for each 500 ml. bottle.

$$CDK4 \; \frac{1.86 \times 10E6 \times 500 \times 3}{1 \times 10^8} = 28 \text{ ml of virus for each 500 ml. bottle.}$$

The viruses were mixed together before addition to the cultures, and the cultures returned to the roller rig 28° C.

After 3 days (72 hrs.) post infection the 5 Liters of culture was harvested. The total cell count at harvest was 1.58×10E6 cells/ml.(99% viable). The cells were spun out at 2500 rpm, 30 mins., 4° C. in Heraeus Omnifuge 2.0 RS in 250 mls. lots. The supernatant was discarded.

20 pellets of ~4×10E8 cells/pellet were snap frozen in $LN_2$ and stored at −80° C. in CCRF cold room. The SF21 cells were then hypotonically lysed by resuspending in lysis buffer (50 mM HEPES pH 7.5, 10 mM magnesium chloride, 1 mM DTT, 10 mM glycerophosphate, 0.1 mM PMSF, 0.1 mM sodium fluoride, 0.1 mM sodium orthovanadate, 5 ug/ml aprotinin, 5 ug/ml leupeptin and 20% w/v sucrose), and adding ice cold deionised water. After centrifugation, the supernatant was loaded onto a Poros HQ/M 1.4/100 anion exchange column (PE Biosystems, Hertford, UK). CDK4 and Cyclin D1 were coeluted with 375 mM NaCl in lysis buffer, and their presence checked by western blot, using suitable anti-CDK4 and anti-Cyclin D1 antibodies (obtained from Santa Cruz Biotechnology, California, US). p16 Control (Nature 366:704–707; 1993: Serrano M. Hannon G J. Beach D)

p16 (the natural inhibitor of CDK4/Cyclin D1) was amplified from HeLa cDNA (Hela cells obtained from ATCC CCL2, human epitheloid carcinoma from cervix; Cancer Res. 12: 264, 1952), cloned into pTB 375 NBSE which had a 5' His tag, and transformed using standard techniques into BL21 (DE3) pLysS cells (obtained from Promega; Ref. Studier F. W. and Moffat B. A., J. Mol. Biol., 189, 113, 1986). A 1 liter culture was grown to the appropriate OD then induced with IPTG to express p16 overnight. The cells were then lysed by sonication in 50 mM sodium phoshate, 0.5 M sodium chloride, PMSF, 0.5 µg/mL leupeptin and 0.5 µg/mL aprotinin. The mixture was spun down, the supernatant added to nickel chelate beads and mixed for 1½ hours. The beads were washed in sodium phosphate, NaCl pH 6.0 and p16 product eluted in sodium phosphate, NaCl pH 7.4 with 200 mM imidazole.

The pTB NBSE was constructed from pTB 375 NBPE as follows:

pTB375

The background vector used for generation of pTB 375 was pZEN0042 (see UK patent 2253852) and contained the tetA/tetR inducble tetracycline resistance sequence from plasmid RP4 and the cer stability sequence from plasmid pKS492 in a pAT153 derived background. pTB375 was generated by the addition of an expression cassette consisting of the T7 gene 10 promoter, multiple cloning site and T7 gene 10 termination sequence. In addition, a terminator sequence designed to reduce transcriptional readthrough from the background vector was included upstream of the expression cassette.

pTB 375 NBPE

The unique EcoRI restriction site present in pTB 375 was removed. A new multiple cloning site containing the recognition sequences for the restriction enzymes NdeI, BamHI, PstI and EcoRI was introduced into pTB 375 between the NdeI and BamHI sites destroying the original BamHI site present in pTB 375.

pTB 375 NBSE

A new multiple cloning site containing the recognition sequences for the restriction enzymes NdeI, BamHI, SmaI and EcoRI was introduced into pTB 375 NBPE between the NdeI and EcoRI sites. The oligonucleotide containing these restriction sites also contained 6 histidine codons located between the NdeI and BamHI sites in the same reading frame as the inititiator codon (ATG) present within the NdeI site.

By analogy to the above, assays designed to assess inhibition of CDK2 and CDK6 may be constructed. CDK2 (EMBL Accession No. X62071) may be used together with Cyclin A or Cyclin E (see EMBL Accession No. M73812), and further details for such assays are contained in PCT International Publication No. WO99/21845, the relevant Biochemical & Biological Evaluation sections of which are hereby incorporated by reference.

If using CDK2 with Cyclin E partial co-purification may be achieved as follows: Sf21 cells are resuspended in lysis buffer (50 mM Tris pH 8.2, 10 mM $MgCl_2$, 1 mM DTT, 10 mM glycerophosphate, 0.1 mM sodium orthovanadate, 0.1 mM NaF, 1 mM PMSF, 1 ug/ml leupeptin and 1 ug/ml aprotinin) and homogenised for 2 minutes in a 10 ml Dounce homgeniser. After centrifugation, the supernatant is loaded onto a Poros HQ/M 1.4/100 anion exchange column (PE Biosystems, Hertford, UK). CDK2 and Cyclin E are coeluted at the beginning of a 0–1 M NaCl gradient (run in lysis buffer minus protease inhibitors) over 20 column volumes. Co-elution is checked by western blot using both anti-CDK2 and anti-Cyclin E antibodies (Santa Cruz Biotechnology, California, US).

FAK3 Kinase Inhibition Assay

This assay determines the ability of a test compound to inhibit tyrosine kinase activity of human Focal Adhesion Kinase (FAK).

DNA encoding FAK is obtained by total gene synthesis (Edwards M, International Biotechnology Lab 5(3), 19–25, 1987) or by cloning. These are then expressed in a suitable expression system to obtain polypeptide with tyrosine kinase activity. For example, FAK, obtained by expression of recombinant protein in insect cells, was found to display intrinsic tyrosine kinase activity.

FAK (full length human cDNA described by Andre et al (Biochemical and Biophysical Research Communications, 1993, 190 (1): 140–147; EMBL/GenBank Accession Number L05186)) was modified such that the resulting protein when translated had a 6-histidine tag at the N-terminus immediately preceding the start methionine. Active FAK protein has been previously expressed in a baculovirus system using a similar N-terminal 6-histidine tag (Protein Expression And Purification, 1996, 7: 12–18). The human FAK cDNA was cloned into the baculovirus transplacement vector, pFastbac 1 (Life Technologies), and the recombinant construct was co-transfected into insect cells (for example *Spodoptera frugiperda* 21(Sf21)) with viral DNA to prepare recombinant baculovirus (details of the methods for the assembly of recombinant DNA molecules and the preparation and use of recombinant baculovirus can be found in standard texts for example Sambrook et al, 1989, Molecular cloning—A Laboratory Manual, 2nd edition, Cold Spring Harbour Laboratory Press and O'Reilly et al, 1992, Baculovirus Expression Vectors—A Laboratory Manual, W.H. Freeman and Co, New York. Details specific to the use of the pFastbac ('Bac to Bac') system are provided in Anderson et al., 1995, FOCUS (Life Technologies Bulletin Magazine), 17, p53.)

For expression of biologically active human FAK protein, Sf21 cells were infected with plaque-pure FAK recombinant virus at a multiplicity of infection of 3 and harvested 48 hours later. Harvested cells were washed with ice cold phosphate buffered saline solution (PBS) (10 mM sodium phosphate pH7.4, 138 mM sodium chloride, 2.7 mM potassium chloride) then resuspended in ice cold lysis buffer (50 mM HEPES pH7.5, 1 mM Dithiothreitol, 100 uM Sodium Fluoride, 100 uM Sodium Orthovanadate, 10 mM Glycerophosphate, 100 uM Phenylmethylsulphonylfluoride (PMSF), 5 ug/ml Aprotinin, 5 ug/ml Leupeptin, 1% Tween; the PMSF being added just before use from a freshly-prepared 100 mM solution in methanol) using 250 ul lysis buffer per 10 million cells. The suspension was then incubated on ice for 15 minutes and centrifuged for 10 minutes at 13,000 rpm at 4° C. The supernatant (enzyme stock) was removed and aliquots made which were snap frozen in liquid nitrogen and then stored at −70° C. For a typical batch, stock enzyme was diluted 1 in 250 with enzyme diluent ((100 mM HEPES pH 7.4, 0.2 mM Dithiothreitol, 200 uM Sodium Orthovanadate, 0.1% Triton X-100) and 50 ml of freshly diluted enzyme was used for each assay well (see FAK3 protocol, below).

FAK3: In vitro Enzyme Assay Protocol

A stock of substrate solution was prepared from a random copolymer containing tyrosine, for example Poly (Glu, Ala, Tyr) 6:3:1 (Sigma P3899), stored as 1 mg/ml stock in PBS at −20° C. and diluted 1 in 500 with PBS for plate coating.

On the day before the assay 100 μl of diluted substrate solution was dispensed into all wells of assay plates (Maxisorp 96 well immunoplates Life technologies, Cat. No. 439454A) which were sealed with plate sealers and left overnight at 4° C.

On the day of the assay the substrate solution was discarded and the assay plate wells were washed once with 200 ul PBST (PBS containing 0.05% v/v Tween 20) and once with 200 ul 50 mM Hepes pH7.4.

Test compounds were made up as 10 mM or 30 mM stocks in DMSO and then further diluted in glass distilled water diluted to a concentration 10 fold higher than the final assay concentration. 10 μl of diluted compound was transferred to wells in the washed assay plates. "No compound" control wells contained 10 ul glass distilled water instead of compound.

Forty microliters of 25 mM manganese chloride containing 6.25 μM adenosine-5'-triphosphate (ATP) was added to all test wells. To start the reactions 50 μl of freshly diluted enzyme was added to each well and the plates were incubated at 23C for 90 minutes. Then the reaction was stopped by adding 100 ul of PBS containing 20 mM EDTA. The liquid was then discarded and the wells were washed twice with PBST.

One hundred microliters of mouse HRP-linked anti-phosphotyrosine antibody (Santa Cruz, Product SC 7020-HRP), diluted 1 in 1500 with PBST containing 0.5% w/v bovine serum albumin (BSA), was added to each well and the plates were incubated for 1 hour at room temperature before discarding the liquid and washing the wells twice with 200 ul PBST. One hundred microliters of 2,2'-azino-bis(3-ethylbenzthiazoline-6-sulphonic acid) (ABTS) solution, freshly prepared using one 50 mg ABTS tablet (Boehringer 1204 521) in 50 ml freshly prepared 50 mM phosphate-citrate buffer pH5.0+0.03% sodium perborate (made with 1 phosphate citrate buffer with sodium perborate (PCSB) capsule (Sigma P4922) per 100 ml distilled water), was added to each well. Plates were then incubated for 20–60 minutes at room temperature until the absorbance value of the "no compound" control wells, measured at 405 nm using a plate reading spectrophotometer, was approximately 1.0.

Dose response curves were generated from the absorbance readings using Origin Software. Compounds were ranked for potency using the Inhibitory Concentration 50 (IC50), as defined by Origin Software analysis.

Although the pharmacological properties of the compounds of the formula (I) or (I') vary with structural change, in general activity possessed by compounds of the formula (I) or (I') in the above assays may be demonstrated at $IC_{50}$ concentrations or doses in the range 250 μM to 1 nM.

When tested in the above in vitro assay the CDK4 inhibitory activity of Example 5 was measured as $IC_{50}$=0.02 μM. When tested in the above in vitro assay the FAK inhibitory activity of Example 3 was measured as $IC_{50}$= 0.553 μM.

The in-vivo activity of the compounds of the present invention may be assessed by standard techniques, for example by measuring inhibition of cell growth and assessing cytotoxicity. For example, further details may be found in the following references:

a) Attenution of the Expression of the Focal Adhesion Kinase induces Apoptosis in Tumor Cells. Xu L-h et al. Cell Growth & Differentiation (1996) 7, p413–418;

b) The COOH-Terminal Domain of the Focal Adhesion Kinase Induces Loss of Adhesion and Cell Death in Human Tumour Cells. Xu L-h et al. Cell Growth & Differentiation (1998) 9, p999–1005;

c) Inhibition of pp125-FAK in Cultured Fibroblasts Results in Apoptosis. Hungerford J. E et al. The Journal of Cell Biology (1996) 135, p1383–1390;

d) Inhibition of Focal Adhesion Kinase (FAK) Signalling in Focal Adhesions Decreases Cell Motility and Proliferation. Gilmore A. P and Romer L. H. Molecular Biology of the Cell (1996) 7, p1209–1224.

Inhibition of cell growth may be measured by staining cells with Sulforhodamine B (SRB), a fluorescent dye that stains proteins and therefore gives an estimation of amount of protein (i.e. cells) in a well (see Boyd, M. R. (1989) Status of the NCI preclinical antitumour drug discovery screen. Prin. Prac Oncol 10:1–12). Thus, the following details are provided of measuring inhibition of cell growth:

Cells were plated in appropriate medium in a volume of 100 μl in 96 well plates; media was Dulbecco's Modified Eagle media for MCF-7, SK-UT-1B and SK-UT-1. The cells were allowed to attach overnight, then inhibitor compounds were added at various concentrations in a maximum concentration of 1% DMSO (v/v). A control plate was assayed to give a value for cells before dosing. Cells were incubated at 37° C., (5% CO2) for three days.

At the end of three days TCA was added to the plates to a final concentration of 16% (v/v). Plates were then incubated at 4° C. for 1 hour, the supernatant removed and the plates washed in tap water. After drying, 100 μl SRB dye (0.4% SRB in 1% acetic acid) was added for 30 minutes at 37° C. Excess SRB was removed and the plates washed in 1% acetic acid. The SRB bound to protein was solubilised in 10 mM Tris pH7.5 and shaken for 30 minutes at room temperature. The ODs were read at 540 nm, and the concentration of inhibitor causing 50% inhibition of growth was determined from a semi-log plot of inhibitor concentration versus absorbance. The concentration of compound that reduced the optical density to below that obtained when the cells were plated at the start of the experiment gave the value for toxicity.

Typical $IC_{50}$ values for compounds of the invention when tested in the SRB assay are in the range 1 mM to 1 nM.

According to a further aspect of the invention there is provided a pharmaceutical composition which comprises a pyrimidine derivative of the formula (I) or (I'), or a pharmaceutically acceptable salt or in vivo hydrolysable ester thereof, as defined hereinbefore in association with a pharmaceutically acceptable diluent or carrier.

The composition may be in a form suitable for oral administration, for example as a tablet or capsule, for parenteral injection (including intravenous, subcutaneous, intramuscular, intravascular or infusion) as a sterile solution, suspension or emulsion, for topical administration as an ointment or cream or for rectal administration as a suppository.

In general the above compositions may be prepared in a conventional manner using conventional excipients.

The pyrimidine will normally be administered to a warm-blooded animal at a unit dose within the range 5–5000 mg per square meter body area of the animal, i.e. approximately 0.1–100 mg/kg, and this normally provides a therapeutically-effective dose. A unit dose form such as a tablet or capsule will usually contain, for example 1–250 mg of active ingredient. Preferably a daily dose in the range of 1–50 mg/kg is employed. However the daily dose will necessarily be varied depending upon the host treated, the particular route of administration, and the severity of the illness being treated. Accordingly the optimum dosage may be determined by the practitioner who is treating any particular patient.

According to a further aspect of the present invention there is provided a pyrimidine derivative of the formula (I) or (I'), or a pharmaceutically acceptable salt or in vivo hydrolysable ester thereof, as defined hereinbefore for use in a method of treatment of the human or animal body by therapy.

We have found that the pyrimidine derivatives defined in the present invention, or a pharmaceutically acceptable salt or in vivo hydrolysable ester thereof, are effective cell cycle inhibitors (anti-cell proliferation agents), which property (without being bound by theory) is believed to arise from their CDK inhibitory properties. The compounds are also effective inhibitors of FAK. Accordingly the compounds of the present invention are expected to be useful in the treatment of diseases or medical conditions mediated alone or in part by CDK and/or FAK enzymes, i.e. the compounds may be used to produce a CDK inhibitory effect in a warm-blooded animal in need of such treatment. Thus the compounds of the present invention provide a method for treating the proliferation and/or migration of malignant cells characterised by inhibition of CDK and/or FAK enzymes, i.e. the compounds may be used to produce an anti-proliferative/migration effect mediated alone or in part by the inhibition of CDKs and/or FAK. The compounds may also be useful as FAK inhibitors by inducing cell-death (apoptosis). Such a pyrimidine derivative of the invention is expected to possess a wide range of anti-cancer properties as CDKs and/or FAK have been implicated in many common human cancers such as leukaemia and breast, lung, colon, rectal, stomach, prostate, bladder, pancreas and ovarian cancer. Thus it is expected that a pyrimidine derivative of the invention will possess anti-cancer activity against these cancers. It is in addition expected that a pyrimidine derivative of the present invention will possess activity against a range of leukaemias, lymphoid malignancies and solid tumours such as carcinomas and sarcomas in tissues such as the liver, kidney, prostate and pancreas. In particular such compounds of the invention are expected to slow advantageously the growth of primary and recurrent solid tumours of, for example, the colon, breast, prostate, lungs and skin. More particularly such compounds of the invention, or a pharmaceutically acceptable salt or in vivo hydrolysable ester thereof, are expected to inhibit the growth of those primary and recurrent solid tumours which are associated with CDKs and/or FAK, especially those tumours which are significantly dependent on CDKs and/or FAK for their growth and spread, including for example, certain tumours of the colon, breast, prostate, lung, vulva and skin.

It is further expected that a pyrimidine derivative of the present invention will possess activity against other cell-proliferation/migration diseases in a wide range of other disease states including leukemias, fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation.

Thus according to this aspect of the invention there is provided a pyrimidine derivative of the formula (I) or (I'), or a pharmaceutically acceptable salt or in vivo hydrolysable ester thereof, as defined hereinbefore for use as a medicament; and the use of a pyrimidine derivative of the formula (I) or (I'), or a pharmaceutically acceptable salt or in vivo hydrolysable ester thereof, as defined hereinbefore in the manufacture of a medicament for use in the production of an anti-cancer, cell cycle inhibitory (anti-cell-proliferation) effect and/or FAK inhibitory (anti-cell migration and/or apoptosis inducing) effect in a warm-blooded animal such as man. Particularly, a cell cycle inhibitory effect is produced at the S or G1-S phase by inhibition of CDK2, CDK4 and/or CDK6, especially CDK4 and CDK6.

According to a further feature of this aspect of the invention there is provided a method for producing an anti-cancer, cell cycle inhibitory (anti-cell-proliferation) effect and/or FAK inhibitory (anti-cell migration and/or apoptosis inducing) effect in a warm-blooded animal, such as man, in need of such treatment which comprises administering to said animal an effective amount of a pyrimidine derivative as defined immediately above. Particularly, an inhibitory effect is produced at the S or G1-S phase by inhibition of CDK2, CDK4 and/or CDK6, especially CDK4 and CDK6.

As stated above the size of the dose required for the therapeutic or prophylactic treatment of a particular cell-proliferation disease will necessarily be varied depending on the host treated, the route of administration and the severity of the illness being treated. A unit dose in the range, for example, 1–100 mg/kg, preferably 1–50 mg/kg is envisaged.

The CDK and/or FAK inhibitory activity defined hereinbefore may be applied as a sole therapy or may involve, in addition to a compound of the invention, one or more other substances and/or treatments. Such conjoint treatment may be achieved by way of the simultaneous, sequential or separate administration of the individual components of the treatment. In the field of medical oncology it is normal practice to use a combination of different forms of treatment to treat each patient with cancer. In medical oncology the other component(s) of such conjoint treatment in addition to the cell cycle inhibitory treatment defined hereinbefore may be: surgery, radiotherapy or chemotherapy. Such chemotherapy may cover three main categories of therapeutic agent:

(i) other cell cycle inhibitory agents that work by the same or different mechanisms from those defined hereinbefore;

(ii) cytostatic agents such as antioestrogens (for example tamoxifen, toremifene, raloxifene, droloxifene, iodoxyfene), progestogens (for example megestrol acetate), aromatase inhibitors (for example anastrozole, letrazole, vorazole, exemestane), antiprogestogens, antiandrogens (for example flutamide, nilutamide, bicalutamide, cyproterone acetate), LHRH agonists and antagonists (for example goserelin acetate, luprolide), inhibitors of testosterone 5α-dihydroreductase (for example finasteride), anti-invasion agents (for example metalloproteinase inhibitors like marimastat and inhibitors of urokinase plasminogen activator receptor function) and inhibitors of growth factor function, (such growth factors include for example platelet derived growth factor and hepatocyte growth factor such inhibitors include growth factor antibodies, growth factor receptor antibodies, tyrosine kinase inhibitors and serine/threonine kinase inhibitors); and
(iii) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); antimitotic agents (for example vinca alkaloids like vincrisitine and taxoids like taxol, taxotere); topoisomerase inhibitors (for example epipodophyllotoxins like etoposide and teniposide, amsacrine, topotecan). According to this aspect of the invention there is provided a pharmaceutical product comprising a pyrimidine derivative of the formula (I) or (I') as defined hereinbefore and an additional anti-tumour substance as defined hereinbefore for the conjoint treatment of cancer. An anti-emetic may also be usefully administered, for example when using such conjoint treatment as described above.

In addition to their use in therapeutic medicine, the compounds of formula (I) or (I') and their pharmaceutically acceptable salts are also useful as pharmacological tools in the development and standardisation of in vitro and in vivo test systems for the evaluation of the effects of inhibitors of cell cycle activity in laboratory animals such as cats, dogs, rabbits, monkeys, rats and mice, as part of the search for new therapeutic agents.

In the above other, pharmaceutical composition, process, method, use and medicament manufacture features, the alternative and preferred embodiments of the compounds of the invention described herein also apply.

The invention will now be illustrated in the following non limiting Examples, in which standard techniques known to the skilled chemist and techniques analogous to those described in these Examples may be used where appropriate, and in which, unless otherwise stated:

(i) evaporations were carried out by rotary evaporation in vacuo and work up procedures were carried out after removal of residual solids such as drying agents by filtration;
(ii) operations were carried out at ambient temperature, typically in the range 18–25° C. and in air unless stated, or unless the skilled person would otherwise operate under an atmosphere of an inert gas such as argon;
(iii) column chromatography (by the flash procedure) and medium pressure liquid chromatography (MPLC) were performed on Merck Kieselgel silica (Art. 9385) or on Merck Lichroprep RP-18 (Art. 9303) reversed-phase silica, obtained from E. Merck, Darmstadt, Germany; bond elute chromatography was performed using Varian Mega Bond Elut cartridges (10 g, order code 1225-6034), obtained from Varian Sample Preparation Products, California, USA;
(iv) yields are given for illustration only and are not necessarily the maximum attainable;
(v) the structures of the end products of the formula (I) were generally confirmed by nuclear (generally proton) magnetic resonance (NMR) and mass spectral techniques; proton magnetic resonance chemical shift values were measured in deuterated DMSO-$d_6$ (unless otherwise stated) on the delta scale (ppm downfield from tetramethylsilane) using a Varian Gemini 2000 spectrometer operating at a field strength of 300 MHz, or a Bruker AM250 spectrometer operating at a field strength of 250 MHz; and peak multiplicities are shown as follows: s, singlet; d, doublet; dd, double doublet; t, triplet; tt, triple triplet; q, quartet; tq, triple quartet; m, multiplet; br, broad; mass spectrometry (MS) was performed by electrospray on a VG platform;
(vi) intermediates were not generally fully characterised and purity was assessed by thin layer chromatography (TLC), HPLC, infra-red (IR), MS or NMR analysis;
(vii) where solutions are dried magnesium sulphate was the drying agent;
(viii) the following abbreviations may be used hereinbefore or hereinafter:

| DCM | dichloromethane; |
|---|---|
| DMF | N,N-dimethylformamide; |
| DMSO | dimethylsulphoxide; |
| NMP | N-methylpyrrolidin-2-one; |

EXAMPLE 1

2-{4-[2-Hydroxy-3-(N,N-dimethylamino)propoxy]anilino}-4-(indolin-1-yl)pyrimidine A hot solution of 4-[2-hydroxy-3-(N,N-dimethylamino)propoxy]aniline hydrochloride (Method 1, 219 mg, 0.77 mmol) in methanol (2 ml) was added to a solution of 2-chloro-4-(indolin-1-yl)pyrimidine (Method 3, 200 mg, 0.86 mmol) in ii-butanol (20 ml). The mixture was heated at 100° C. for 18 hours and silica (1 g) was added. Volatile material was removed by evaporation and the residue was purified by column chromatography, eluting with 0–5% 2.0M methanolic ammonia solution in DCM, to give the product as a colourless solid (201 mg, 61%). NMR: 2.19 (s, 6H), 2.21–2.3 (m, 1H), 2.3–2.4 (m, 1H), 3.1–3.25 (m, 2H), 3.8–4.1 (m, 5H), 5.75 (m, 1H), 6.2 (m, 2H), 6.8–6.9 (m, 3H), 7.0–7.1 (m, 1H), 7.15–7.25 (m, 1H), 7.5–7.6 (m, 2H), 8.05–8.1 (m, 1H), 8.3–8.4 (m, 1H), 8.95 (s, 1H); MS (MH$^+$): 406.5.

EXAMPLES 2–5

The following compounds were prepared by an analogous method to that described in Example 1, using 4-[2-hydroxy-3-(N,N-dimethylamino)propoxy]aniline hydrochloride Method 1) and the appropriate 2-chloro-4-(indolin-1-yl)pyrimidine (Methods 4–7):

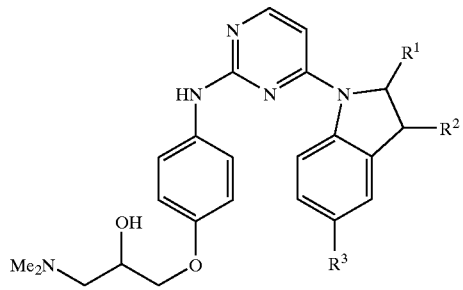

| Ex | R¹ | R² | R³ | NMR | MS (MH⁺) |
|---|---|---|---|---|---|
| 2 | Me | H | H | 1.15–1.25(d, 3H), 2.19(s, 6H), 2.21–2.3(m, 1H), 2.3–2.4(m, 1H), 3.19–3.25(m, 3H), 3.8–4.0(m, 3H), 4.6–4.7(m, 1H), 5.75(m, 1H), 6.2(m, 2H), 6.8–6.9(m, 3H), 7.0–7.1(m, 1H), 7.15–7.25(m, 1H), 7.5–7.6(m, 2H), 8.05–8.1(m, 1H), 8.3–8.4(m, 1H), 8.95(s, 1H) | 420 |
| 3 | H | H | Br | 2.19(s, 6H), 2.21–2.3(m, 1H), 2.3–2.4(m, 1H), 3.1–3.25(m, 2H), 3.8–4.1(m, 4H), 5.75(m, 1H), 6.2(m, 1H), 6.8–6.9(m, 2H), 7.15–7.25(m, 1H), 7.5–7.6(m, 2H), 8.05–8.1(m, 1H), 8.3–8.4(m, 1H), 9.05(s, 1H) | 484, 486 |
| 4 | H | H | —COMe | 2.19(s, 6H), 2.21–2.3(m, 1H), 2.3–2.45(m, 1H), 3.1–3.25(m, 2H), 3.8–4.0(m, 3H), 4.05–4.15(m, 2H), 4.75(m, 1H), 6.25(m, 1H), 6.9–6.9(m, 2H), 7.5–7.6(m, 2H), 7.75–7.8(m, 2H), 8.05–8.1(m, 1H), 8.4–8.5(m, 1H), 8.95(s, 1H) | 448 |
| 5 | Me | Me | H | 1.0–1.1(m, 3H), 1.15–1.25(m, 1H), 1.25–1.4(m, 3H), 2.19(s, 6H), 2.21–2.3(m, 1H), 2.3–2.4(m, 1H), 3.5–3.6(m, 1H), 3.8–4.1(m, 5H), 5.75(m, 1H), 6.3(m, 1H), 6.8–6.9(m, 2H), 6.9–7.0(m, 1H), 7.0–7.1(m, 1H), 7.15–7.25(m, 1H), 7.5–7.6(m, 2H), 8.05–8.1(m, 1H), 8.1–8.2(m, 1H), 8.95(s, 1H) | 433 |

EXAMPLE 6

4-(1,2,3,4-Tetrahydroquinolin-1-yl)-2-{4-[2-hydroxy-3-(N,N-dimethylamino)propoxy]anilino}pyrimidine Using an analogous method to that described in Example 1, but starting from 4-[2-hydroxy-3-(N,N-dimethylamino)propoxy]aniline hydrochloride (Method 1) and 2-chloro-4-(1,2,3,4-tetrahydroquinolin-1-yl)pyrimidine (Method 8), the product was obtained. NMR: 1.8–2.0 (m, 2H), 2.19 (s, 6H), 2.2–2.3 (m, 1H), 2.3–2.45 (m, 1H), 2.7–2.8 (m, 2H), 3.7–3.9 (m, 5H), 5.7 (m, 1H), 6.35 (m, 2H), 6.8 (m, 2H), 7.0–7.05 (m, 1H), 7.1–7.2 (m, 2H), 7.35–7.4 (m, 1H), 7.5–7.6 (m, 2H), 7.9–8.0 (m, 2H), 8.95 (s, 1H); MS (MH⁺): 420.5.

EXAMPLES 7–9

The following compounds were prepared by an analogous method to that described in Example 1, using 4-[2-hydroxy-3-(N,N-dimethylamino)propoxy]aniline hydrochloride (Method 1) and the appropriate 4-substituted 2-chloropyrimidine (obtained as described in PCT Int. Appl. WO 9911657 and Eur. J. Med. Chem., 1991, 26, 729–33):

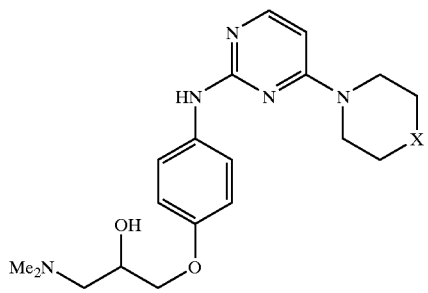

| Ex | X | NMR | MS (MH+) |
|---|---|---|---|
| 7 | NCO$_2$Bu-t | 1.42(s, 9H), 2.18(s, 6H), 2.33(m, 2H), 3.39(m, 4H), 3.57 (m, 4H), 3.82(m, 3H), 6.18(d, 1H), 6.82(d, 2H), 7.53(d, 2H), 7.93(d, 1H), 8.81(s, 1H) | 473.6 |
| 8[1] | NH | 2.83(m, 6H), 3.98(m, 8H), 4.30(m, 1H), 6.62(d, 1H), 7.00 (d, 2H), 7.42(d, 2H), 8.03(d, 1H), 9.73(1H), 9.97(br, 1H) | 373.4 |
| 9[2] | O | 2.82(d, 6H), 3.35(m, 5H), 3.74(m, 8H), 3.96(m, 2H), 4.28 (m, 1H), 6.59(d, 1H), 6.99(d, 2H), 7.40(d, 2H), 7.97(d, 1H) | 374.4 |

[1]Obtained as a side product from Example 7 by filtration of the precipitated hydrochloride salt from the reaction mixture.
[2]Isolated by filtration of the precipitated hydrochloride salt from the reaction mixture.

EXAMPLES 10–11

The following compounds were prepared by an analogous method to that described in Example 1, using 4-[2-hydroxy-3-(N,N-dimethylamino)propoxy]aniline hydrochloride (Method 1) and the appropriate 2-chloro-5-halo-4-(indolin-1-yl)pyrimidine (Methods 9–10):

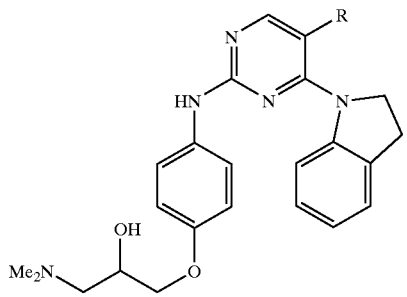

| Ex | R | NMR | MS (MH+) |
|---|---|---|---|
| 10 | Cl | 2.18(s, 6H), 2.34(m, 2H), 3.13(m, 2H), 3.82(m, 3H), 4.23(m, 2H), 6.79(d, 2H), 6.92(t, 1H), 7.09(t, 1H), 7.22(d, 1H), 7.34(d, 1H), 7.50(d, 2H), 8.22(s, 1H), 9.24(s, 1H) | 440.4, 442.5 |
| 11 | F | 2.18(s, 6H), 2.34(m, 2H), 3.17(m, 2H), 3.82(m, 3H), 4.24(m, 2H), 4.76(m, 1H), 6.82(d, 2H), 6.93(t, 1H), 7.07(t, 1H), 7.22(d, 1H), 7.50(d, 2H), 7.98(d, 1H), 8.14(d, 1H), 9.02(s, 1H) | 424.4 |

EXAMPLES 12–14

The following compounds were prepared by an analogous method to that described in Example 1, using 4-[2-hydroxy-3-(N,N-dimethylamino)propoxy]aniline hydrochloride (Method 1) and the appropriate 4-substituted 2-chloro-5-halo-pyrimidine (Methods 12–14):

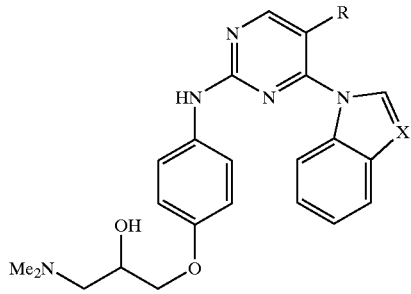

| Ex | X | R | NMR | MS (MH⁺) |
|---|---|---|---|---|
| 12[1] | N | Br | 2.2(s, 6H), 2.4(m, 2H), 3.9(m, 3H), 4.9(d, 1H), 7.05(d, 2H), 7.2(t, 1H), 7.3(t, 1H), 7.4(d, 2H), 7.7(d, 1H), 8.0(d, 1H), 8.6 (s, 1H), 8.9(s, 1H), 9.4(s, 1H) | 483, 485 |
| 13 | CH | Br | 2.2(s, 6H), 2.4(m, 2H), 3.9(m, 3H), 4.8(d, 1H), 6.9(d, 2H), 7.2(m, 3H), 7.55(d, 2H), 7.6(d, 1H), 7.7(d, 1H), 7.8(d, 1H), 8.8(s, 1H), 9.8(s, 1H) | 482, 484 |
| 14 | CH | Cl | 2.2(s, 6H), 2.4(m, 2H), 3.9(m, 3H), 4.8(d, 1H), 6.8(d, 1H), 6.9(d, 2H), 7.3(m, 2H), 7.6(d, 2H), 2.7(d, 1H), 7.8(m, 2H), 8.7(s, 1H), 9.9(s, 1H) | 438, 440 |

[1]Reaction time reduced to 2 hours.

EXAMPLE 15

2-{4-[2-Hydroxy-3-(N,N-dimethylamino)propoxy] anilino}-4-(indol-1-yl)-5-methylpyrimidine Sodium hydride (60% dispersion in oil; 116 mg, 2.9 mmol) was added to a solution of indole (340 mg, 2.9 mmol) in NMP (2 ml) at 0° C. The mixture was stirred at 0° C. for 10 minutes and then added dropwise to a cold (0° C.) solution of 2,4-dichloro-5-methylpyrimidine (489 mg, 3.0 mmol) in NMP (3 ml). The mixture was stirred at 0° C. for 3 hours and then 4-[3-(N,N-dimethyl)amino-2-hydroxypropoxy]aniline hydrochloride (Method 1, 500 mg, 1.76 mmol) was added. The mixture was heated at 100° C. overnight and then silica (2 g) was added. Volatile material was removed by evaporation and the residue was purified by column chromatography, eluting with 0–5% 2.0M methanolic ammonia solution in DCM, to give the product as a white solid (166 mg, 13%). NMR: 2.1 (m, 9H), 2.3 (m, 2H), 3.9 (m, 3H), 4.8 (d, 1H), 6.85 (d, 1H), 6.9 (d, 2H), 7.2 (m, 2H), 7.6 (m, 5H), 8.5 (s, 1H), 9.5 (s, 1H); MS (MH⁺): 418.

EXAMPLE 16

6-{4-[2-Hydroxy-3-(N,N-dimethylamino)propoxy] anilino}-4-(indolin-1-yl)pyrimidine A solution of 4-chloro-6-(indolin-1-yl)pyrimidine (Method 15, 220 mg, 0.95 mmol) and 4-[2-hydroxy-3-(N, N-dimethylamino)propoxy]aniline hydrochloride (Method 1, 229 mg, 0.81 mmol) in NMP (5 ml) was heated to 150° C. for 1 hour. Sodium bicarbonate solution (20 ml) was added and the mixture was extracted with ethyl acetate (20 ml). The extracts were washed with water (2×10 ml) and dried. Silica (1 g) was added and volatile material removed by evaporation. The residue was purified by column chromatography, eluting with 0–8% 2.0M methanolic ammonia solution in DCM, to give the product as a colourless solid (108 mg). NMR: 2.18 (s, 6H), 2.32 (m, 2H), 3.17 (m, 2H), 3.86 (m, 5H), 4.78 (d, 1H), 5.96 (s, 1H), 6.85 (m, 3H), 7.16 (m, 2H), 7.44 (d, 2H), 8.26 (m, 2H), 9.02 (s, 1H); MS (MH⁺): 406.

EXAMPLES 17–18

The following compounds were prepared by an analogous method to that described in Example 16, using 4-[2-hydroxy-3-(N,N-dimethylamino)propoxy]aniline hydrochloride (Method 1) and the appropriate 4-chloro-6-(indolin-1-yl)pyrimidine (Methods 16–17):

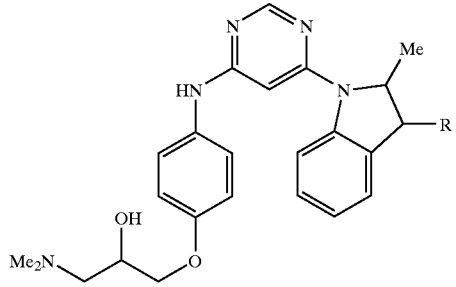

| Ex | R | NMR | MS (MH+) |
|---|---|---|---|
| 17 | H | 1.21(d, 3H), 2.19(s, 6H),), 2.32(m, 2H), 2.65(m, 1H), 3.37(m, 1H), 3.84(m, 3H), 4.57(m, 1H), 4.78(br, 1H), 6.11(s, 1H), 6.88 (m, 3H), 7.18(m, 2H), 7.43(d, 2H), 8.04(d, 1H), 8.26(s, 1H), 9.00 (s, 1H) | 420.4 |
| 18 | Me | 1.04(d, 3H), 1.27(d, 3H), 2.17(s, 6H), 2.32(m, 3H), 2.70(m, 1H), 3.82(m, 3H), 4.58(m, 1H), 4.77(m, 1H), 6.12(s, 1H), 6.88(m, 3H), 7.16(m, 2H), 7.43(m, 2H), 7.97(d, 1H), 8.26(s, 1H), 8.98(s, 1H) | 434.5 |

Preparation of Starting Materials

The starting materials for the Examples above are either commercially available or are readily prepared by standard methods from known materials. For example, the following reactions are an illustration, but not a limitation, of some of the starting materials used in the above reactions.

Method 1

4-[2-Hydroxy-3-(N,N-dimethylamino)propoxy] aniline Hydrochloride

A solution of 4-[2-hydroxy-3-(N,N-dimethylamino) propoxy]nitrobenzene (Method 2, 3.75 g) in ethanol (40 ml) was catalytically hydrogenated over 10% palladium-on-carbon (0.4 g) overnight. The catalyst was removed by filtration through diatomaceous earth and the filtrate was concentrated. The residue was dissolved in diethyl ether containing a small amount of isopropanol and ethereal hydrogen chloride (1M, 16 ml) was added. Diethyl ether was removed by evaporation and the solid residue was suspended in isopropanol. The mixture was heated on a steam bath for several minutes and then allowed to cool. The insoluble solid was collected by filtration, washed with isopropanol and ether, and dried to give the product (3.04 g, 72.4%). NMR: 2.80 (s, 6H), 3.15 (m, 2H), 3.88 (m, 2H), 4.25 (m, 1H), 5.93 (br S, 1H), 6.88 (m, 4H); MS (MH+): 211; $C_{11}H_{18}N_2O_2 \cdot 1.6HCl$ requires: C; 49.2, H; 7.4, N; 10.4, Cl; 21.7%; found: C; 49.2, H; 7.2, N; 10.1; Cl; 19.1%.

Method 2

4-[2-Hydroxy-3-(N,N-dimethylamino)propoxy] nitrobenzene 4-(2,3-Epoxypropoxy)nitrobenzene (obtained as described in Synthetic Communications, 1994, 24, 833; 4.3 g) was dissolved in methanol (30 ml) and DMF (10 ml). A solution of dimethylamine in methanol (2M, 17 ml) was added and the mixture was stirred overnight. Volatile material was removed by evaporation and the residue was partitioned between saturated sodium bicarbonate (100 ml) and ethyl acetate (100 ml). The organic layer was separated and washed with saturated sodium chloride (2×100 ml) and dried. Concentration gave the product as an oil that slowly crystallised under high vacuum (4.79 g, 89.9%). NMR (CDCl₃): 2.33 (s, 6H), 2.98 (m, 1H), 2.54 (m, 1H), 4.00 (m, 3 H), 7.00 (d, 2H), 8.20 (d, 2H); MS (MH+): 241.

Method 3

2-Chloro-4-(indolin-1-yl)pyrimidine

A solution of 2,4-dichloropyrimidine (596 mg, 4.0 mmol), indoline (0.45 ml, 4.0 mmol) and N,N-diisopropylethylamine (0.69 ml, 4.0 mmol) in n-butanol (20 ml) was heated at 100° C. for 18 hours. Silica (3 g) was added and volatile material was removed by evaporation. The residue was purified by column chromatography, eluting with 0–40% ethyl acetate/isohexane, to give the product as a colourless solid (460 mg, 50%). NMR (CDCl₃): 3.2 (t, 2H), 4.0–4.1 (t, 2H), 6.5 (d, 1H), 7.0–7.1 (m, 1H) 7.2–7.3 (m, 2H), 8.2 (m, 1H), 8.3–8.4 (m, 1H); MS (MH+): 232.7.

Methods 4–7

The following compounds were prepared by an analogous method to that described in Method 3, starting from 2,4-dichloropyrimidine and the appropriate substituted indoline:

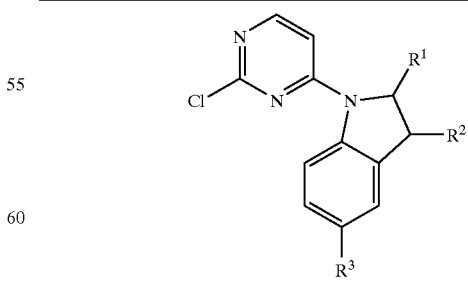

| Method | R¹ | R² | R³ | MS (MH+) |
|---|---|---|---|---|
| 4 | Me | H | H | 246.2, 248.2 |
| 5 | H | H | Br | 310.1, 312.1 |

-continued

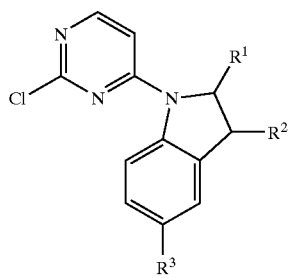

| Method | R¹ | R² | R³ | MS (MH⁺) |
|---|---|---|---|---|
| 6 | H | H | COMe | 274.1, 276.2 |
| 7 | Me | Me | H | 260.5, 262.5 |

Method 8

2-Chloro-4-(1,2,3,4-tetrahydroquinolin-1-yl)pyrimidine

Using an analogous method to that described in Method 3, but starting from 2,4-dichloropyrimidine and 1,2,3,4-tetrahydroquinoline, the product was obtained. MS (MH⁺): 246, 248.

Methods 9–10

The following compounds were prepared by an analogous method to that described in Method 3, starting from indoline and the appropriate 2,4-dichloro-5-halopyrimidine (commercially available or obtained as described in Method 11):

| Method | R | MS (MH⁺) |
|---|---|---|
| 9 | Cl | 266.0, 268.1, 270.1 |
| 10 | F | 250.1, 252.1 |

Method 11

2,4,5-Trichloropyrimidine

5-Chlorouracil (10.0 g, 68.5 mmol) was dissolved in phosphorus oxychloride (60 ml) and phosphorus pentachloride (16.0 g, 77.0 mmol) was added. The mixture was heated under reflux for 16 hours, left to cool and then poured slowly into water (200 ml) with vigorous stirring. The mixture was stirred for 1.5 hours and then ethyl acetate (250 ml) was added. The organic layer was separated and the aqueous layer was extracted with a further portion of ethyl acetate (250 ml). The combined extracts were washed with saturated sodium bicarbonate (200 ml) and saturated sodium chloride solution (200 ml), and then dried. Volatile material was removed by evaporation and the residue was purified by column chromatography, eluting with DCM, to give the product as a yellow liquid (6.37 g, 51%). NMR (CDCl₃): 8.62 (s, 1H); MS (MH⁺): 182, 184, 186.

Method 12

5-Bromo-2-chloro-4-(benzimidazol-1-yl)pyrimidine

Sodium hydride (60% dispersion in oil; 110 mg, 2.75 mmol) was added to a solution of benzimidazole (295 mg, 2.5 mmol) in DMF (6 ml) at 0° C. The mixture was stirred at 0° C. for 10 minutes and then added dropwise to a cold (0° C.) solution of 5-bromo-2,4-dichloropyrimidine (712 mg, 3.14 mmol) in DMF (6 ml). The mixture was stirred for at 0° C. for 2 hours and then ethyl acetate (20 ml) and water (20 ml) were added. The organic phase was separated and dried and volatile material was removed by evaporation. The residue was purified by column chromatography, eluting with 20% ethyl acetate/DCM, to give the product as a white solid (500 mg, 52%). NMR: 7.4 (m, 2H), 7.8 (m, 2H), 8.8 (s, 1H), 9.3 (s, 1H); MS (MH⁺): 309, 311.

Methods 13–14

The following compounds were prepared by an analogous method to that described in Method 12, starting from indole and the appropriate 2,4-dichloro-5-halopyrimidine (commercially available or obtained as described in Method 11):

| Method | R | MS (MH⁺) |
|---|---|---|
| 13 | Br | 308, 310 |
| 14¹ | Cl | |

¹Used without purification or characterisation.

Methods 15–17

The following compounds were prepared by an analogous method to that described in Method 3, starting from 4,6-dichloropyrimidine and the appropriate indoline and carrying out the reaction at 125° C. for 1 hour:

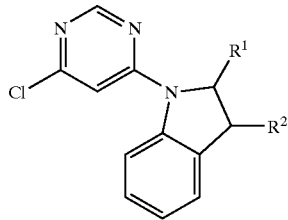

| Method | R¹ | R² | MS (MH⁺) |
|---|---|---|---|
| 15 | H | H | 232.1, 234.1 |
| 16 | Me | H | 246.1, 248.1 |
| 17 | Me | Me | 260.2, 262.2 |

EXAMPLE 19

The following illustrate representative pharmaceutical dosage forms containing the compound of formula (I) or (I'), or a pharmaceutically acceptable salt or in vivo hydrolysable ester thereof (hereafter compound X), for therapeutic or prophylactic use in humans:

| (a): Tablet I | mg/tablet |
|---|---|
| Compound X | 100 |
| Lactose Ph. Eur | 182.75 |
| Croscarmellose sodium | 12.0 |
| Maize starch paste (5% w/v paste) | 2.25 |
| Magnesium stearate | 3.0 |

| (b): Tablet II | mg/tablet |
|---|---|
| Compound X | 50 |
| Lactose Ph. Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c): Tablet III | mg/tablet |
|---|---|
| Compound X | 1.0 |
| Lactose Ph. Eur | 93.25 |
| Croscarmellose sodium | 4.0 |
| Maize starch paste (5% w/v paste) | 0.75 |
| Magnesium stearate | 1.0 |

| (d): Capsule | mg/capsule |
|---|---|
| Compound X | 10 |
| Lactose Ph. Eur | 488.5 |
| Magnesium stearate | 1.5 |

| (e): Injection I | (50 mg/ml) |
|---|---|
| Compound X | 5.0% w/v |
| 1 M Sodium hydroxide solution | 15.0% v/v |
| 0.1 M Hydrochloric acid | (to adjust pH to 7.6) |
| Polyethylene glycol 400 | 4.5% w/v |
| Water for injection | to 100% |

| (f): Injection II | 10 mg/ml |
|---|---|
| Compound X | 1.0% w/v |
| Sodium phosphate BP | 3.6% w/v |
| 0.1 M Sodium hydroxide solution | 15.0% v/v |
| Water for injection | to 100% |

| (g): Injection III | (1 mg/ml, buffered to pH6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection | to 100% |

Note
The above formulations may be obtained by conventional procedures well known in the pharmaceutical art. The tablets (a)–(c) may be enteric coated by conventional means, for example to provide a coating of cellulose acetate phthalate.

What we claim is:
1. A pyrimidine compound of the formula (I):

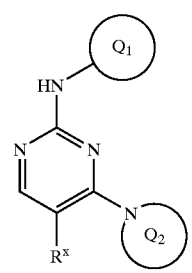

(I)

wherein:
$R^x$ is selected from hydrogen, halo, hydroxy, nitro, amino, $C_{1-3}$alkylamino, di-[$C_{1-3}$alkyl]amino, cyano, trifluoromethyl, trichloromethyl, $C_{1-3}$alkyl [optionally substituted by 1 or 2 substituents independently selected from halo, cyano, amino, $C_{1-3}$alkylamino, di-[$C_{1-3}$alkyl]amino, hydroxy and trifluoromethyl], $C_{3-5}$alkenyl [optionally substituted by up to three halo substituents, or by one trifluoromethyl substituent], $C_{3-5}$alkynyl, $C_{1-3}$alkoxy, —SH, —S—$C_{1-3}$alkyl, carboxy, $C_{1-3}$alkoxycarbonyl;

$Q_1$ is phenyl, and $Q_1$ bears on an available carbon atom not adjacent to the —NH— link one substituent of the formula (Ia), and —NQ₂ (defined hereinbelow) may optionally bear on any available carbon atom further substituents of the formula (Ia):

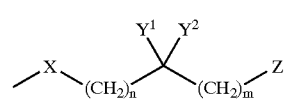

(Ia)

wherein:
X is —CH₂—, —O—, —NH—, —NR^y— or —S— [wherein $R^y$ is $C_{1-4}$alkyl, optionally substituted by one substituent selected from halo, amino, cyano, $C_{1-4}$alkoxy or hydroxy];
$Y^1$ is H, $C_{1-4}$alkyl or as defined for Z;
$Y^2$ is H or $C_{1-4}$alkyl;
Z is $R^a$O—, $R^bR^cN$—, $R^dS$—, $R^eR^fNNR^g$—, a nitrogen linked heteroaryl or a nitrogen linked heterocycle [wherein said heterocycle is optionally substituted on a ring carbon or a ring nitrogen by $C_{1-4}$alkyl or $C_{1-4}$alkanoyl] wherein $R^a$, $R^b$, $R^c$, $R^d$, $R^e$, $R^f$ and $R^g$ are independently selected from hydrogen, $C_{1-4}$alkyl, $C_{2-4}$alkenyl, $C_{3-8}$cycloalkyl, and wherein said $C_{1-4}$alkyl and $C_{2-4}$alkenyl are optionally substituted by one or more phenyl;

n is 1, 2 or 3;

m is 1, 2 or 3; and

—$NQ_2$ is an unquaternised N-linked 5-, 6- or 7-membered monocyclic heterocyclic moiety having one nitrogen heteroatom and optionally having a further one or two heteroatoms selected from nitrogen, oxygen and sulphur or —$NQ_2$ is an unquaternised N-linked 8-, 9- or 10-membered bicyclic heterocyclic moiety having one or two nitrogen heteroatoms and optionally having a further one or two heteroatoms selected from nitrogen, oxygen and sulphur and wherein if said heterocyclic moiety contains an —NH— moiety that nitrogen may be optionally substituted by a group selected from $C_{1-6}$alkyl, $C_{1-6}$alkanoyl, $C_{1-6}$alkylsulphonyl, $C_{1-6}$alkoxycarbonyl, benzyl, benzoyl or phenylsulphonyl;

and $Q_1$ and —$NQ_2$ may optionally and independently bear on any available carbon atom up to four substituents independently selected from halo, hydroxy, thio, nitro, carboxy, cyano, $C_{2-4}$alkenyl [optionally substituted by up to three halo substituents, or by one trifluoromethyl substituent], $C_{2-4}$alkynyl, $C_{1-5}$alkanoyl, $C_{1-4}$alkoxycarbonyl, $C_{1-6}$alkyl, hydroxy-$C_{1-3}$alkyl, fluoro-$C_{1-4}$alkyl, amino-$C_{1-3}$alkyl, $C_{1-4}$alkylamino-$C_{1-3}$alkyl, di-[$C_{1-4}$alkyl]amino-$C_{1-3}$alkyl, cyano-$C_{1-4}$alkyl, $C_{2-4}$alkanoyloxy-$C_{1-4}$-alkyl, $C_{1-4}$alkoxy-$C_{1-3}$alkyl, carboxy-$C_{1-4}$alkyl, $C_{1-4}$alkoxycarbonyl-$C_{1-4}$alkyl, carbamoyl-$C_{1-4}$alkyl, N-$C_{1-4}$alkylcarbamoyl-$C_{1-4}$alkyl, N,N-di-[$C_{1-4}$alkyl]-carbamoyl-$C_{1-4}$alkyl, pyrrolidin-1-yl-$C_{1-3}$alkyl, piperidin-1-yl-$C_{1-3}$alkyl, piperazin-1-yl-$C_{1-3}$alkyl, morpholino-$C_{1-3}$alkyl, thiomorpholino-$C_{1-3}$alkyl, imidazo-1-yl-$C_{1-3}$alkyl, piperazin-1-yl, morpholino, thiomorpholino, $C_{1-4}$alkoxy, cyano-$C_{1-4}$alkoxy, carbamoyl-$C_{1-4}$alkoxy, N-$C_{1-4}$alkylcarbamoyl- $C_{1-4}$alkoxy, N,N-di-[$C_{1-4}$alkyl]-carbamoyl $C_{1-4}$alkoxy, 2-aminoethoxy, 2-$C_{1-4}$alkylaminoethoxy, 2-di- [$C_{1-4}$alkyl]aminoethoxy, $C_{1-4}$alkoxycarbonyl-$C_{1-4}$alkoxy, halo-$C_{1-4}$alkoxy, 2-hydroxyethoxy, $C_{2-4}$alkanoyloxy-$C_{2-4}$alkoxy, 2-$C_{1-4}$alkoxyethoxy, carboxy-$C_{1-4}$alkoxy, 2-pyrrolidin-1-yl-ethoxy, 2-piperidino-ethoxy, 2-piperazin-1-yl-ethoxy, 2-morpholino-ethoxy, 2-thiomorpholino-ethoxy, 2-imidazo-1-yl-ethoxy, $C_{3-5}$alkenyloxy, $C_{3-5}$alkynyloxy, $C_{1-4}$alkylthio, $C_{1-4}$alkylsulphinyl, $C_{1-4}$alkylsulphonyl, hydroxy $C_{2-4}$alkylthio, hydroxy$C_{2-4}$alkylsulphinyl, hydroxy $C_{2-4}$alkylsulphonyl, ureido ($H_2N$—CO—NH—), $C_{1-4}$alkylNH—CO—NH—, di-[$C_{1-4}$alkyl]N—CO—NH—, $C_{1-4}$alkylNH—CO—N[$C_{1-4}$alkyl]-, di-[$C_{1-4}$alkyl]N—CO—N[$C_{1-4}$alkyl]-, carbamoyl, N-[$C_{1-4}$alkyl]carbamoyl, N,N-di-[$C_{1-4}$alkyl]carbamoyl, amino, $C_{1-4}$alkylamino, di-[$C_{1-4}$alkyl]amino, $C_{2-4}$alkanoylamino, sulphamoyl, N-($C_{1-4}$alkyl)sulphamoyl, N,N-di-($C_{1-4}$alkyl)sulphamoyl, and also independently, or where appropriate in addition to, the above optional substituents, $Q_1$ and —$NQ_2$ may optionally and independently bear on any available carbon atom up to two further substituents independently selected from $C_{3-8}$cycloalkyl, phenyl-$C_{1-4}$alkyl, phenyl-$C_{1-4}$alkoxy, phenylthio, phenyl, naphthyl, benzoyl, phenoxy, benzimidazol-2-yl, and a 5- or 6-membered aromatic heterocycle (linked via a ring carbon atom and having one to three heteroatoms independently selected from oxygen, sulphur and nitrogen); wherein said naphthyl, phenyl, benzoyl, phenoxy, 5- or 6-membered aromatic heterocyclic substituents and the phenyl group in said phenyl-$C_{1-4}$alkyl, phenylthio and phenyl-$C_{1-4}$alkoxy substituents may optionally bear one or two substituents independently selected from halo, $C_{1-4}$alkyl and $C_{1-4}$alkoxy;

or a pharmaceutically acceptable salt or in vivo hydrolysable ester thereof.

2. A pyrimidine compound according to claim 1 wherein $R^x$ is hydrogen, fluoro, chloro, bromo or methyl; or a pharmaceutically acceptable salt or in vivo hydrolysable ester thereof.

3. A pyrimidine compound according to claim 1 wherein —$NQ_2$ is indoline, piperazine, morpholine, 1,2,3,4-tetrahydroquinolinyl, benzimidazole or indole; or a pharmaceutically acceptable salt or in vivo hydrolysable ester thereof.

4. A pyrimidine compound according to claim 1 wherein the substituent of formula (Ia) is 3-dimethylamino-2-hydroxypropoxy; or a pharmaceutically acceptable salt or in vivo hydrolysable ester thereof.

5. A pyrimidine compound according to claim 1 wherein —$NQ_2$ is optionally substituted by halo, $C_{1-5}$alkanoyl or $C_{1-4}$alkyl; and if a heterocyclic moiety in —$NQ_2$ contains an —NH— moiety that nitrogen is unsubstituted or substituted by $C_{1-6}$alkoxycarbonyl; or a pharmaceutically acceptable salt or in vivo hydrolysable ester thereof.

6. A pyrimidine compound according to claim 1 wherein the substituent of formula (Ia) is para to the —NH—; or a pharmaceutically acceptable salt or in vivo hydrolysable ester thereof.

7. A pyrimidine compound according to claim 1 which is:

2-{4-[2-hydroxy-3-(N,N-dimethylamino)propoxy]anilino}-4-(2,3-dimethylindolin-1-yl)pyrimidine;

or a pharmaceutically acceptable salt or in vivo hydrolysable ester thereof.

8. A process for preparing a pyrimidine compound of the formula (I) as defined in claim 1, which comprises of:

a) reacting a pyrimidine of formula (II):

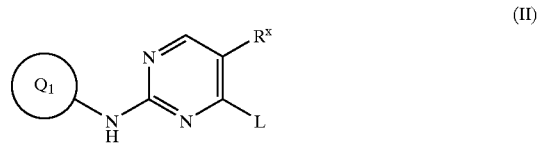

(II)

wherein L is a displaceable group, with a compound of formula (III):

(III)

b) reaction of a pyrimidine of formula (IV):

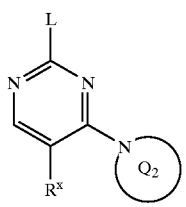

(IV)

wherein L is a displaceable group, with a compound of formula (V):

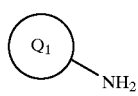

(V)

c) for compounds of formula (I) where n is 1, 2 or 3, m=1 $Y^2$ is H and $Y^1$ is OH, $NH_2$ or SH, by reaction of a three-membered heteroalkyl ring containing compound of formula (VI):

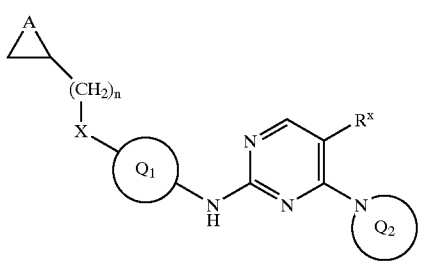

(VI)

wherein A is O, S or NH;
with a nucleophile of formula (VII):

Z—D   (VII)

wherein D is H or a suitable counter-ion;

d) for compounds of formula (I) where X is oxygen, by reaction of an alcohol of formula (VIII):

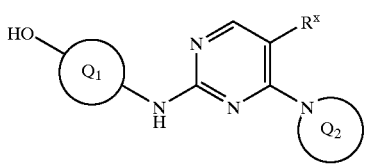

(VIII)

with an alcohol of formula (IX):

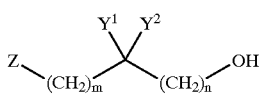

(IX)

e) for compounds of formula (I) wherein X is —CH$_2$—, —O—, —NH— or —S—, $Y^1$ is OH, $Y^2$ is H and m is 2 or 3; reaction of a compound of formula (X):

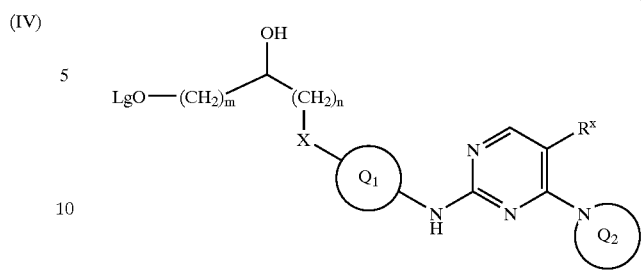

(X)

wherein LgO is a leaving group; with a nucleophile of formula (VII);

f) or compounds of formula (I) wherein X is —CH$_2$—, —O—, —NH— or —S—, $Y^1$ is H, $Y^2$ is H, n is 1, 2 or 3 and m is 1, 2 or 3; reaction of a compound of formula (XI):

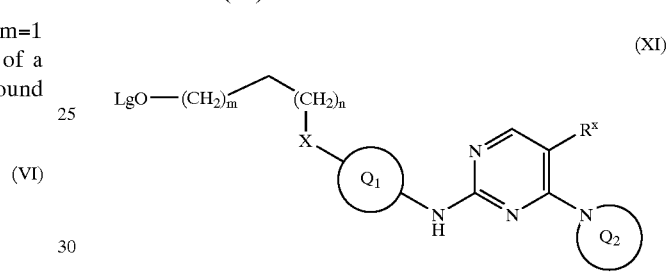

(XI)

wherein LgO is a leaving group; with a nucleophile of formula (VII);

g) for compounds of formula (I) wherein X is —O—, —NH— or —S—, $Y^1$ is H, $Y^2$ is H, n is 1, 2 or 3 and m is 1, 2 or 3; reaction of a compound of formula (XII):

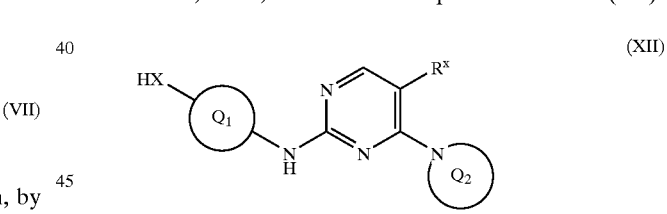

(XII)

with a compound of formula (XIII)

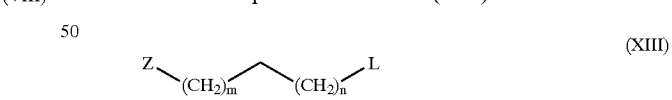

(XIII)

wherein L is a displaceable group;

h) for compounds of formula (I) in which Z is HS—, by conversion of a thioacetate group in a corresponding compound;

and thereafter if necessary:
i) converting a compound of the formula (I) into another compound of the formula (I);
ii) removing any protecting groups;
iii) forming a pharmaceutically acceptable salt or in vivo hydrolysable ester.

9. A pharmaceutical composition which comprises a pyrimidine compound of the formula the formula (I) according to any one of claims 1 to 7, or a pharmaceutically acceptable salt or an in vivo hydrolysable ester thereof, and a pharmaceutically-acceptable diluent or carrier.

10. A method for producing a FAK enzyme inhibitory effect in a warm-blooded animal in need of such treatment, which comprises administering to said animal an effective amount of a compound of formula (I) or a pharmaceutically acceptable salt or in vivo hydrolysable ester thereof as claimed in any one of claims 1–7.

11. A method for producing a selective CDK2, CDK4 or CDK6 enzyme inhibitory effect in a warm-blooded animal in need of such treatment, which comprises administering to said animal an effective amount of a compound of formula (I) or a pharmaceutically acceptable salt or in vivo hydrolysable ester thereof as claimed in any one of claims 1–7.

* * * * *